US007038113B1

(12) United States Patent
Dixon et al.

(10) Patent No.: US 7,038,113 B1
(45) Date of Patent: May 2, 2006

(54) GENETIC MANIPULATION OF ISOFLAVONOIDS

(75) Inventors: Richard A. Dixon, Ardmore, OK (US); Christopher L. Steele, Manlius, NY (US)

(73) Assignee: The Samuel Roberts Noble Foundation, Inc., Ardmore, OK (US)

( * ) Notice: Subject to any disclaimer, the term of this patent is extended or adjusted under 35 U.S.C. 154(b) by 0 days.

(21) Appl. No.: 09/936,190

(22) PCT Filed: Mar. 8, 2000

(86) PCT No.: PCT/US00/05915

§ 371 (c)(1),
(2), (4) Date: Dec. 9, 2001

(87) PCT Pub. No.: WO00/53771

PCT Pub. Date: Sep. 14, 2000

Related U.S. Application Data

(60) Provisional application No. 60/123,267, filed on Mar. 8, 1999.

(51) Int. Cl.
| C12N 15/29 | (2006.01) |
| C12N 15/63 | (2006.01) |
| C12N 15/82 | (2006.01) |
| A01H 5/00 | (2006.01) |
| A01H 5/10 | (2006.01) |

(52) U.S. Cl. .................. 800/312; 800/278; 800/298
(58) Field of Classification Search ............... 800/278, 800/298, 312; 536/23.1, 23.2, 23.6
See application file for complete search history.

(56) References Cited

FOREIGN PATENT DOCUMENTS

| WO | WO9615239 | 5/1996 |
| WO | WO9919493 | 4/1999 |

OTHER PUBLICATIONS

Siminszky B. et al. PNAS, Feb. 1999, vol. 96, pp. 1750-1755.*
Liu C. et al. The Plant Journal, 2003; vol. 36 pp. 471-484.*
Liu C. et al. PNAS, 2002, vol. 99, No. 22; pp. 14578-14583.*
Adlercreutz, et al., 1991, "Urinary excretion of lignans and isoflavonoid phytoestrogens in Japanese men and women consuming a traditional Japanese diet," *Am J Clin Nutr* 54:1093-1100.
Akashi, et al, 1998, "Identification of a cytochrome P450 cDNA encoding (2S)-flavanone 2-hydroxylase of licorice (*Glycyrrhiza echinata* L.: Fabaceae) which represents licodione synthase and flavone synthase II," *FEBS Letters* 431: 287-290.

Akashi, T., et al., 1999, "Cloning and Functional Expression of a Cytochrome P450 cDNA Encoding 2-Hydroxyisoflavanone Synthase Involved in Biosynthesis of the Isoflavonoid Skeleton in Licorice," *Plant Physiology*, 121:821-828.
Akiyama, et al., 1987, "Genistein, a specific inhibitor of tyrosine-specific protein kinases," *J Biol Chem* 262: 5592-559.
Angell, S. M. and D. C. Baulcombe, 1997, "Consistent gene silencing in transgenic plants expressing a replicating potato virus X RNA," *EMBO J* 16:3675-3684.
Arora, et al., 1998, "Antioxidant activities of isoflavones and their biological metabolites in a lipsomal system," *Arch Biochem Biophys* 356: 133-141.
Bhattacharyya, M. K. and E. W. B. Ward, 1987, "Biosynthesis and metabolism of glyceollin I in soybean hypocotyls following wounding or inoculation with *Phytophthora megasperma* f. sp. *glycinea*," *Physiol and Mol Plant Pathology* 31: 387-405.
Bourque, J.E., 1995, "Antisense strategies for genetic manipulation in plants," *Plant Science* 105:125-149.
Clough, S.J. and Bent, A.F., 1998, "Floral dip: a simplified method for *Agrobacterium*-mediated transformation of *Arabidopsis thaliana*", *Plant J* 16:735-74.
Colliver, S.P., et al., 1997, "Differential modification of flavonoid and isoflavonoid biosynthesis with an antisense chalcone synthase construct in trasgenic *Lotus corniculatus*," *Plant Molecular Biology*, 35: 509-522.
Coward, et al., 1993, "Genistein, daidzein, and their β-glycoside conjugates: antitumor isoflavones in soybean foods from American and Asian diets," *J Agricultural and Food Chemistry* 41: 1961-1967.
Dakora, et al., 1993, "Common bean root exudates contain elevated levels of daidzein and coumestrol in response to *Rhizobium* inoculation," *Mol Plant-Microbe Interact* 6: 665-668.

(Continued)

*Primary Examiner*—Amy J. Nelson
*Assistant Examiner*—Russell Kallis
(74) *Attorney, Agent, or Firm*—Fulbright & Jaworski L.L.P.

(57) ABSTRACT

Soybean and *Medicago truncatula* CYP93C genes have been isolated which encode a cytochrome P450 that can catalyze the aryl migration of a flavanone to yield an isoflavanone intermediate or an isoflavone. Plants can now be genetically engineered to produce isoflavones that provide potential human health benefits and increase disease resistance in plants. Isoflavones can now be produced in transgenic plants species in which isoflavones do not naturally occur, i.e., in species other than legumes. Alternatively, introducing infection-inducible isoflavonoid biosynthesis into non-legumes qualitatively complements these plants phytoalexin defenses against microbial pathogens, whereas over-expression of the isoflavonoid pathway in legumes quantitatively increases this defense response. Finally, modifying the extend of production of isoflavonoids in legume roots positively impacts nodulation efficiency and therefore plant yield.

25 Claims, 15 Drawing Sheets

OTHER PUBLICATIONS

Dixon, R. A. and N. L. Paiva, 1995, "Stress-induced phenylpropanoid metabolism," *Plant Cell* 7: 1085-1097.

Dixon, R., et al., 1995, "The isoflavonoid phytoalexin pathway: From enzymes to genes to transcription factors," *Physiologia Plantarum*, 93:385-392.

Dixon, R.A., Blyden, E.R., Robbins, M.P., van Tunen, A.J. and Mol, J.N.M., 1988, "Comparative biochemistry of chalcone isomerases." *Phytochemistry* 27: 2801-2808.

Dixon, R.A., et al., 1999 "Molecular controls for isoflavonoid biosynthesis in relation to plant and human health," *Phytochemicals in Human Health Protection, Nutrition and Plant Defense*, Romeo, ed., Kluwer Academic/Plenum Publishers, New York; pp. 133-159.

Draper, et al., 1997, "Phytoestrogens reduce bone loss and bone resorption in oophorectomized rats," *J Nutr* 127: 1795-1799.

Graham, T.L., 1991, "Flavonoid and isoflavonoid distribution in developing soybean seeding tissues and in seed and root exudates." *Plant Physiol* 95: 594-603.

Graham, T.L., 1998, "Flavonoid and flavonol glycoside metabolism in *Arabidopsis*". *Plant Physiol Biochem* 36: 135-144.

Hadwiger, L. A. and D. M. Webster, 1984, "Phytoelexin production in five cultivars of pea differentially resistant to three races of *Pseudomonas syringae* pv. *pisi*," *Phytopathology* 74: 1312-1314.

Hagmann, M. and H. Grisebach, 1984, "Enzymatic rearrangement of flavanone to isoflavone," *FEBS Letters* 175: 199-202.

Hakamatsuka, et al., 1991, "P-450-dependent oxidative rearrangement in isoflavone biosynthesis: reconstitution of P-450 and NADPH:P450 reductase," *Tetrahedron* 47: 5969-5978.

Hakamatsuka, et al., 1998, "Purification of 2-hydroxyisoflavanone dehydratase from the cell cultures of *Pueraria lobata*," *Phytochemistry* 49: 497-505.

Hashim, et al., 1990, "Reaction Mechanism of oxidative rearrangement of flavanone in isoflavone biosynthesis," *FEBS Letters* 271: 219-222.

Horsch, et al., 1985, "A simple and general method for transferring genes into plants," *Science* 227:1229-1231.

Jung, W., et al., 2000, "Identification and expession of isoflavone synthase, the key enzyme for biosynthesis of isoflavones in legumes," *Nature Biotechnology* 18: 206-212.

Kape, et al., 1992, "Legume root metabolites and VA-mycorrhiza development," *J Plant Physiol* 141: 54-60.

Kessmann, et al., 1990, "Stress responses in alfalfa (*Medicago sativa* L.) III. Induction of medicarpin and cytochrome P450 enzyme activities in elicitor-treated cell suspension cultures and protoplasts," *Plant Cell Reports* 9: 38-41.

Keung, et al., 1995, "Daidzin suppresses ethanol consumption by Syrian golden hamsters without blocking acetaldehyde metabolism," *Proc Natl Acad Sci USA* 92: 8990-8993.

Keung, W. M. and B. L. Vallee, 1993, "Daidzin: A potent, selective inhibitor of human mitochondrial aldehyde dehydrogenase," *Proc Natl Acad Sci USA* 90: 1247-1251.

Kirikae, et al., 1993, "Biosynthesis of a dibenzoylmethane, licodione, in cultured alfalfa cells induced by yeast extract," *Biosci Biotech Biochem* 57: 1353-1354.

Klein, et al., 1988, "Stable genetic transformation of intact *Nicotiana* cells by the particle bombardment process," *Proc Natl Acad Sci USA* 85:8502-8505.

Kochs, G. and H. Grisebach, 1986, "Enzymic synthesis of isoflavones," *European J Biochem* 155: 311-318.

Kochs, G. and H. Grisebach, 1987, "Induction and characterization of a NADPH-dependent flavone synthase from cell cultures of soybean," *Z. Naturforsch* 42C: 343-348.

Kosslak, et al., 1987, "Induction of *Bradyrhizobium japonicum* common nod genes by isoflavones isolated from *Glycine max*," *Proc Natl Acad Sci USA* 84: 7428-7432.

Köster, J. and W. Barz, 1981, "UDP-Glucose: isoflavone 7-O-glucosyltransferase from roots of chick pea (*Cicer arietinum* L.)." *Arch Biochem Biophys* 212: 98-104.

Lee, et al., 1991, "Dietary effects on breast-cancer risk in Singapore," *Lancet* 337: 1197-1200.

Long, et al., 1985, "Further studies on the relationship between glyceollin accumulation and the resistance of soybean leaves to *Pseudomonas syringae* pv. *glycinea*," *Phytopathology* 75: 235-239.

Martens, S. and G. Forkmann, "Cloning and expression of flavone synthase II from Gerbera hybrids," *Plant J* 20: 616-618.

Martin, et al., 1996, "Interactions between phytoestrogens and human sex steroid binding protein," *Life Sciences* 58: 429-436.

Nelson, et al. 1993. "The P450 superfamily update on new sequences, gene mapping, accession numbers, early trivial names of enzymes, and nomenclature," *DNA Cell Biol* 12:1.

Otani, et al., 1994, "Licodione synthase, a cytochrome P450 monooxygenase catalyzing 2-hydroxylation of 5-deoxyflavanone, in cultured *Glycyrrhiza echinata* L. cells," *Plant Physiol* 105: 1427-1432.

Paiva, N. L. et al., 1994, "Regulation of isoflavonoid metabolism in alfalfa," *Plant Cell, Tissue and Organ Culture*, 38: 213-220.

Pauli, H. H. and T. M. Kutchan, 1998, "Molecular cloning and functional heterologous expression of two alleles encoding (S)-N-methylcoclaurine 3'-hydroxylase (CYP80B1), a new methyl jasmonate-inducible cytochrome P-450-dependent mono-oxygenase of benzylisoquinoline alkaloid biosynthesis," *The Plant J* 13: 793-801.

Rahe, J. E., 1973, "Occurrence and levels of the phytoalexin phaseollin in relation to delimitation at sites of infection of *Phaseolus vulgaris* by *Colletotrichum lindemuthianum*," *Canadian J Botany* 51: 2423-2430.

Sambrook, et al. 1989. *Molecular Cloning. A Laboratory Manual*, 2nd Ed, Cold Spring Harbor Laboratory Press, New York; pp. 7.2-7.87 and 9.2-9.62.

Siminszky, B., Corbin, F.T., Ward, E.R., Fleischmann, T.J. and Dewey, R.E. , 1999, "Expression of a soybean cytochrome P450 monooxygenase cDNA in yeast and tobacco enhances the metabolism of phenylurea herbicides." *Proc. Natl. Acad. Sci. USA* 96: 1750-1755.

Steele, C.L., et al., 1999, "Molecular Characterization of the Enzyme Catalyzing the Aryl Migration Reaction of Isoflavonoid Biosynthesis in Soybean," *Archives of Biochemistry and Biophysics*, 367: 146-150.

Tahara, S. and R. K. Ibrahim, 1995, "Prenylated isoflavonoids—an update," *Phytochemistry* 38: 1073-1094.

Tikkanen, et al., 1998, "Effect of soybean phytoestrogen intake on low density lipoprotein oxidation resistance," *Proc Natl Acad Sci USA* 95: 3106-3110.

Tomonaga, et al., 1992, "Isoflavonoids, genistein, PSI-tectorigenin, and orobol, increase cytoplasmic free calcium in isolated rat hepatocytes," *Biochem Biophys Res Com* 182: 894-899.

Uckun, et al., 1995, "Biotherapy of B-cell precursor leukemia by targeting genistein to CD19-associated tyrosine kinases," *Science* 267: 886-891.

van Buuren, M.L., I.E. Maldonado-Mendoza, A. T. Trieu, L.A. Blaylock, and M.J. Harrison, 1999, "Novel genes induced during an arbuscular mycorrhizal (AM) symbiosis formed between *Medicago truncatula* and *Glomus versiforme*," *Mol. Plant-Microbe Interact*. 12, 171-181.

VanEtten, et al., 1989, "Phytoalexin detoxification: importance for pathogenicity and practical implications," *An Rev Phytopathology* 27: 143-164.

Wagner, et al., 1997, "Dietary soy protein and estrogen replacement therapy improve cardiovascular risk factors and decrease aortic cholesteryl ester content in ovariectomized cynomolgus monkeys," *Metabolism—Clinical and Experimental* 46: 698-705.

Welle, R. and Grisebach, H., 1989, "Phytoalexin synthesis in soybean cells: elicitor induction of reductase involved in biosynthesis of 6'-deoxychalcone." *Arch Biochem Biophys* 272: 97-102.

Xie, et al., 1995, "Rhizobial nodulation factors stimulate mycorrhizal colonization of nodulating and nonnodulating soybeans," *Plant Physiology* 108: 1519-1525.

* cited by examiner

```
   1  GAGCAAAGAT CAAACAAACC AAGGACGAGA ACACGATGTT GCTTGAACTT
  51  GCACTTGGTT TATTGGTTTT GGCTCTGTTT CTGCACTTGC GTCCCACACC
 101  CACTGCAAAA TCAAAGCAC  TTCGCCATCT CCCAAACCCA CCAAGCCCAA
 151  AGCCTCGTCT TCCCTTCATA GGACACCTTC ATCTCTTAAA AGACAAACTT
 201  CTCCACTACG CACTCATCGA CCTCTCCAAA AAACATGGTC CCTTATTCTC
 251  TCTCTACTTT GGCTCCATGC CAACCGTTGT TGCCTCCACA CCAGAATTGT
 301  TCAAGCTCTT CCTCCAAACG CACGAGGCAA CTTCCTTCAA CACAAGGTTC
 351  CAAACCTCAG CCATAAGACG CCTCACCTAT GATAGCTCAG TGGCCATGGT
 401  TCCCTTCGGA CCTTACTGGA AGTTCGTGAG GAAGCTCATC ATGAACGACC
 451  TTCTCAACGC CACCACTGTA AACAAGTTGA GGCCTTTGAG GACCCAACAG
 501  ATCCGCAAGT TCCTTAGGGT TATGGCCCAA GGCGCAGAGG CACAGAAGCC
 551  CCTTGACTTG ACCGAGGAGC TTCTGAAATG GACCAACAGC ACCATCTCCA
 601  TGATGATGCT CGGCGAGGCT GAGGAGATCA GAGACATCGC TCGCGAGGTT
 651  CTTAAGATCT TTGGCGAATA CAGCCTCACT GACTTCATCT GGCCATTGAA
 701  GCATCTCAAG GTTGGAAAGT ATGAGAAGAG GATCGACGAC ATCTTGAACA
 751  AGTTCGACCC TGTCGTTGAA AGGGTCATCA AGAAGCGCCG TGAGATCGTG
 801  AGGAGGAGAA AGAACGGAGA GGTTGTTGAG GGTGAGGTCA GCGGGGTTTT
 851  CCTTGACACT TTGCTTGAAT TCGCTGAGGA TGAGACCATG GAGATCAAAA
 901  TCACCAAGGA CCACATCAAG GGTCTTGTTG TCGACTTTTT CTCGGCAGGA
 951  ACAGACTCCA CAGCGGTGGC AACAGAGTGG GCATTGGCAG AACTCATCAA
1001  CAATCCTAAG GTGTTGGAAA AGGCTCGTGA GGAGGTCTAC AGTGTTGTGG
1051  GAAAGGACAG ACTTGTGGAC GAAGTTGACA CTCAAAACCT TCCTTACATT
1101  AGAGCAATCG TGAAGGAGAC ATTCCGCATG CACCCGCCAC TCCCAGTGGT
1151  CAAAAGAAAG TGCACAGAAG AGTGTGAGAT TAATGGATAT GTGATCCCAG
1201  AGGGAGCATT GATTCTCTTC AATGTATGGC AAGTAGGAAG AGACCCCAAA
1251  TACTGGGACA GACCATCGGA GTTCCGTCCT GAGAGGTTCC TAGAGACAGG
1301  GGCTGAAGGG GAAGCAGGGC TCTTGATCT  TAGGGGACAA CATTTTCAAC
1351  TTCTCCCATT TGGGTCTGGG AGGAGAATGT GCCCTGGAGT CAATCTGGCT
1401  ACTTCGGGAA TGGCAACACT TCTTGCATCT CTTATTCAGT GCTTCGACTT
1451  GCAAGTGCTG GTCCACAAG  GACAGATATT GAAGGGTGGT GACGCCAAAG
1501  TTAGCATGGA AGAGAGAGCC GGCCTCACTG TTCCAAGGGC ACATAGTCTT
1551  GTCTGTGTTC CACTTGCAAG GATCGGCGTT GCATCTAAAC TCCTTTCTTA
1601  ATTAAGATCA TCGTCATCAT CATCATATGT AATATTTACT TTTTGTGTGT
1651  TGATAATCAT CATTTCAATA AGGTCTCATT CATCTACTTT TTATGAAGTA
1701  TATAAGCCCT TCCATGC
```

Fig. 2

```
CYP93C1v2   1 ...MLLELALGLLVLALFLHLRPTPTAKSKALRHLPNPPSPKPRLPFIGH  47
              |.... . | : || || |||| ||| |||
CYP93B1     1 MEPQLVAVSVLVSALICYFFFRPYFHRYGKNL.....PPSPFFRLPIIGH   45

48 LHLLKDKLLHYALIDLSKKHGPLFSLYFGSMPTVVASTPELFKLFLQTHE   97
              :|:| ||| .  .|| ::|||||| |||.  ||||||    |  |||.|
           46 MHML.GPLLHQSFHNLSHRYGPLFSLNFGSVLCVVASTPHFAKQLLQTNE   94

98 ATSFNTRFQTSAIRRLTYDSSVAMVPFGPYWKFVRKLIMNDLLNATTVNK  147
              .|| |  :..|:::|||:||.| |:| ||:|::|| ||:||   ..:|
           95 .LAFNCRIESTAVKKLTYESSLAFAPYGDYWRFIKKLSMNELLGSRSINN  143

148 LRPLRTQQIRKFLRVMAQGAEAQKPLDLTEELLKWTNSTISMMMLGEAEE  197
              . || |: . ||.:.   | |  . ..:|||||| ||. ||.||.|||||
          144 FQHLRAQETHQLLRLLSNRARAFEAVNITEELLKLTNNVISIMMVGEAEE  193

198 IRDIAREVLKIFGEYSLTDFIWPLKHLKVGKYEKRIDDILNKFDPVVERV  247
              ||: |:| .||||:...|||| |  : .  |||:|: :|| .|||:
          194 ARDVVRDVTEIFGEFNVSDFIWLFKKMDLQGFGKRIEDLFQRFDTLVERI  243

248 IKKRREIVR.RRKNGEVVE.GEVSGV..FLDTLLEFAEDETMEIKITKDH  293
              | || :  : ||:||. || |: ||| ||: ||| |||| : |
          244 ISKREQTRKDRRRNGKKGEQGSGDGIRDFLDILLDCTEDENSEIKIQRVH  293

294 IKGLVVDFFSAGTDSTAVATEWALAELINNPKVLEKAREEVYSVVGKDRL  343
              || |:.|||.||||.||:.|||||  ||:  |  ||:| |||:  |||||||
          294 IKALIMDFFTAGTDTTAISTEWALVELVKKPSVLQKVREEIDNVVGKDRL  343

344 VDEVDTQNLPYIRAIVKETFRMHPPLPVVKRKCTEECEINGYVIPEGALI  393
              |:| |  ||||:.||.|||||!:|||.|.|  |:|  ||   ||||| .|:
          344 VEESDCPNLPYLQAILKETFRLHPPVPMVTRRCVAECTVENYVIPEDSLL  393

394 LFNVWQVGRDPKYWDRPSEFRPERFLETGAEGEAGPLDLRGQHFQLLPFG  443
              ||| :||.||:|| | |||||||.   :    .|  .|.||  ||||||||
          394 FVNVWSIGRNPKFWDNPLEFRPERFLKLEGD.SSGVVDVRGSHFQLLPFG  442

444 SGRRMCPGVNLATSGMATLLASLIQCFDLQVLGPQGQILKGGDAKVSMEE  493
              ||||||||| .||   ||  .:|||||  |.||.|:||||   |  :..:|
          443 SGRRMCPGVSLAMQEVPALLGAIIQCFDFHVVGPKGEILKGDDIVINVDE  492

494 RAGLTVPRAHSLVCVPLARIGVASKLLS... 521
              | ||| ||||.||||.||||. |     |
          493 RPGLTAPRAHNLVCVPVDRTSGGGPLKIIEC 523
```

Fig. 3

```
   1    CAACACCTAA GAGTAACTAA TAAGAACTTT CTTTCTACTT CTTAGTATAC
  51    TTAACAACTT AAGTAAATAT ACTACAAAGA AGCTATACAC CATGTTGGTG
 101    GAACTTGCAG TTACTCTATT GCTCATTGCT CTCTTCTTAC ACTTGCGTCC
 151    AACACCTACT GCAAAATCAA AGGCTCTTCG CCACCTTCCA AATCCACCAA
 201    GCCCTAAACC ACGTCTTCCA TTCATAGGTC ATCTTCACCT TTTGGATAAC
 251    CCACTTCTTC ACCACACTCT TATCAAGTTA GGAAAGCGTT ATGGCCCTTT
 301    GTACACTCTT TACTTTGGTT CCATGCCTAC CGTTGTTGCA TCCACTCCTG
 351    ACTTGTTTAA ACTTTTCCTT CAAACCCATG AAGCTACTTC CTTTAACACA
 401    AGATTCCAAA CCTCTGCTAT TAGTCGTCTT ACCTATGACA ACTCTGTTGC
 451    TATGGTTCCA TTTGCACCTT ATTGGAAGTT TATTAGAAAG CTTATCATGA
 501    ACGACTTGCT CAACGCCACC ACTGTTAACA AATTGAGGCC ATTGAGGAGC
 551    CGAGAAATCC TTAAGGTTCT TAAGGTCATG GCTAATAGTG CTGAAACTCA
 601    ACAGCCACTT GATGTCACTG AGGAGCTTCT CAAGTGGACA AACAGCACAA
 651    TCTCTACCAT GATGTTGGGT GAGGCCGAAG AGGTTAGAGA TATTGCTCGT
 701    GATGTTCTTA AGATCTTTGG AGAATATAGT GTTACAAACT TTATTTGGCC
 751    TTTGAACAAG TTTAAGTTTG GAAACTATGA TAAGAGAACT GAGGAGATTT
 801    TCAATAAGTA TGATCCTATC ATTGAAAAGG TTATCAAGAA ACGACAAGAG
 851    ATTGTGAACA AAAGAAAAAA TGGAGAAATC GTAGAAGGCG AGCAGAATGT
 901    TGTTTTTCTT GACACTTTGC TTGAATTTGC ACAAGATGAG ACCATGGAGA
 951    TCAAAATTAC AAAGGAACAA ATCAAGGGTC TTGTTGTGGA TTTTTTCTCT
1001    GCAGGAACAG ACTCCACCGC CGTGTCTACA GAATGGACTT TATCAGAGCT
1051    CATCAATAAT CCTAGAGTGT TGAAGAAAGC TCGAGAGGAG ATTGACTCTG
1101    TTGTGGGAAA AGATAGACTG GTTGATGAAT CAGATGTTCA GAATCTTCCT
1151    TACATTAAAG CCATCGTAAA AGAAGCATTT CGCTTGCACC CACCACTACC
1201    TGTAGTCAAA AGAAAATGTA CACAAGAATG TGAGATCGAC GGGTATGTGG
1251    TTCCAGAAGG AGCACTAATA CTTTTCAATG TCTGGGCAGT GGGAAGAGAC
1301    CCAAAATATT GGGTAAAGCC ATTGGAATTT CGTCCAGAGA GGTTCATAGA
1351    AAATGTTGGT GAAGGTGAAG CAGCTTCAAT TGATCTTAGG GGTCAACATT
1401    TCACACTTCT ACCATTTGGG TCTGGAAGAA GGATGTGTCC TGGAGTCAAT
1451    TTGGCTACTG CAGGAATGGC CACAATGATT GCATCTATTA TCCAATGCTT
1501    CGATCTCCAA GTACCTGGTC AACATGGAGA ATATTGAAT GGTGATTATG
1551    CTAAGGTTAG CATGGAAGAG AGACCTGGTC TCACAGTTCC AAGGGCACAT
1601    AATCTCATGT GTGTTCCTCT TGCAAGAGCT GGTGTCGCAG ATAAACTTCT
1651    TTCCTCCTAA AATATCTTGA GAGGATGAAT CACCAACATA TAGCCTCTCT
1701    TTGGTACTAC AAAATTATGA TGTAATTTTC TTATTTTTTC TGTCACAAAG
1751    GAAGTGTTGT AACTTGTAAT TGCATACAAA ATCTATAAAT TTTATCATCC
1801    TATTCATTAT T
```

Fig. 4

```
mtIFS      1   MLVELAVTLLLIALFLHLRPTPTAKSKALRHLPNPPSPKPRLPFIGHLHL  50
               ||.|||. ||.:||||||||||||||||||||||||||||||||||||||
CYP93C1v2  1   MLLELALGLLVLALFLHLRPTPTAKSKALRHLPNPPSPKPRLPFIGHLHL  50

51  LDNPLLHHTLIKLGKRYGPLYTLYFGSMPTVVASTPDLFKLFLQTHEATS 100
               | . |||: || |  |::|||:.||||||||||||:||||||||||||| 
           51  LKDKLLHYALIDLSKKHGPLFSLYFGSMPTVVASTPELFKLFLQTHEATS 100

101  FNTRFQTSAISRLTYDNSVAMVPFAPYWKFIRKLIMNDLLNATTVNKLRP 150
               |||||||||| |||||.||||||| |||||:|||||||||||||||||||
          101  FNTRFQTSAIRRLTYDSSVAMVPFGPYWKFVRKLIMNDLLNATTVNKLRP 150

151  LRSREILKVLKVMANSAETQQPLDVTEELLKWTNSTISTMMLGEAEEVRD 200
               ||...:| | |:|||  || |.|||.|||||||||||| ||||||||:||
          151  LRTQQIRKFLRVMAQGAEAQKPLDLTEELLKWTNSTISMMMLGEAEEIRD 200

201  IARDVLKIFGEYSVTNFIWPLNKFKFGNYDKRTEEIFNKYDPIIEKVIKK 250
               |||:|||||||||.|.||||| |  | | |:|| ::| ||:||::|:||||
          201  IAREVLKIFGEYSLTDFIWPLKHLKVGKYEKRIDDILNKFDPVVERVIKK 250

251  RQEIVNKRKNGEIVEGEQNVVFLDTLLEFAQDETMEIKITKEQIKGLVVD 300
               |.|||  :|||||:||||  . ||||||||||:|||||||||: |||||||
          251  RREIVRRRKNGEVVEGEVSGVFLDTLLEFAEDETMEIKITKDHIKGLVVD 300

301  FFSAGTDSTAVSTEWTLSELINNPRVLKKAREEIDSVVGKDRLVDESDVQ 350
               |||||||||||.||| |.|||||:||.|||||: ||||||||||| | |
          301  FFSAGTDSTAVATEWALAELINNPKVLEKAREEVYSVVGKDRLVDEVDTQ 350

351  NLPYIKAIVKEAFRLHPPLPVVKRKCTQECEIDGYVVPEGALILFNVWAV 400
               |||||:||||| ||:||||||||||||:||||.|||:||||||||||||  |
          351  NLPYIRAIVKETFRMHPPLPVVKRKCTEECEINGYVIPEGALILFNVWQV 400

401  GRDPKYWVKPLEFRPERFIENVGEGEAASIDLRGQHFTLLPFGSGRRMCP 450
               |||||| :| |||||||:|    ||||  :||||||||||||||||||||
          401  GRDPKYWDRPSEFRPERFLETGAEGEAGPLDLRGQHFQLLPFGSGRRMCP 450

451  GVNLATAGMATMIASIIQCFDLQVPGQHGEILNGDYAKVSMEERPGLTVP 500
               ||||||.||||::||||||||| |  |:|| | ||||||||||| |||||
          451  GVNLATSGMATLLASLIQCFDLQVLGPQGQILKGGDAKVSMEERAGLTVP 500

501  RAHNLMCVPLARAGVADKLLSS 522
               |||.|.|||||||| ||| ||||
          501  RAHSLVCVPLARIGVASKLLS  521
```

Fig. 5

SEQUENCE LISTING

<160> NUMBER OF SEQ ID NOS: 5

<210> SEQ ID NO 1
<211> LENGTH: 1717
<212> TYPE: DNA
<213> ORGANISM: Glycine max
<220> FEATURE:
<221> NAME/KEY: CDS
<222> LOCATION: (36)..(1598)

<400> SEQUENCE: 1

```
gagcaaagat caaacaaacc aaggacgaga acacg atg ttg ctt gaa ctt gca           53
                                        Met Leu Leu Glu Leu Ala
                                          1               5 ctt ggt tta ttg gtt ttg gct ctg ttt ctg cac ttg cgt ccc aca ccc          101
Leu Gly Leu Leu Val Leu Ala Leu Phe Leu His Leu Arg Pro Thr Pro
             10                  15                  20 act gca aaa tca aaa gca ctt cgc cat ctc cca aac cca cca agc cca          149
Thr Ala Lys Ser Lys Ala Leu Arg His Leu Pro Asn Pro Pro Ser Pro
         25                  30                  35 aag cct cgt ctt ccc ttc ata gga cac ctt cat ctc tta aaa gac aaa          197
Lys Pro Arg Leu Pro Phe Ile Gly His Leu His Leu Leu Lys Asp Lys
     40                  45                  50 ctt ctc cac tac gca ctc atc gac ctc tcc aaa aaa cat ggt ccc tta          245
Leu Leu His Tyr Ala Leu Ile Asp Leu Ser Lys Lys His Gly Pro Leu
 55                  60                  65                  70 ttc tct ctc tac ttt ggc tcc atg cca acc gtt gtt gcc tcc aca cca          293
Phe Ser Leu Tyr Phe Gly Ser Met Pro Thr Val Val Ala Ser Thr Pro
                 75                  80                  85 gaa ttg ttc aag ctc ttc ctc caa acg cac gag gca act tcc ttc aac          341
Glu Leu Phe Lys Leu Phe Leu Gln Thr His Glu Ala Thr Ser Phe Asn
             90                  95                 100 aca agg ttc caa acc tca gcc ata aga cgc ctc acc tat gat agc tca          389
Thr Arg Phe Gln Thr Ser Ala Ile Arg Arg Leu Thr Tyr Asp Ser Ser
         105                 110                 115 gtg gcc atg gtt ccc ttc gga cct tac tgg aag ttc gtg agg aag ctc          437
Val Ala Met Val Pro Phe Gly Pro Tyr Trp Lys Phe Val Arg Lys Leu
    120                 125                 130 atc atg aac gac ctt ctc aac gcc acc act gta aac aag ttg agg cct          485
Ile Met Asn Asp Leu Leu Asn Ala Thr Thr Val Asn Lys Leu Arg Pro
135                 140                 145                 150 ttg agg acc caa cag atc cgc aag ttc ctt agg gtt atg gcc caa ggc          533
Leu Arg Thr Gln Gln Ile Arg Lys Phe Leu Arg Val Met Ala Gln Gly
                155                 160                 165 gca gag gca cag aag ccc ctt gac ttg acc gag gag ctt ctg aaa tgg          581
Ala Glu Ala Gln Lys Pro Leu Asp Leu Thr Glu Glu Leu Leu Lys Trp
            170                 175                 180 acc aac agc acc atc tcc atg atg atg ctc ggc gag gct gag gag atc          629
Thr Asn Ser Thr Ile Ser Met Met Met Leu Gly Glu Ala Glu Glu Ile
        185                 190                 195 aga gac atc gct cgc gag gtt ctt aag atc ttt ggc gaa tac agc ctc          677
Arg Asp Ile Ala Arg Glu Val Leu Lys Ile Phe Gly Glu Tyr Ser Leu
    200                 205                 210 act gac ttc atc tgg cca ttg aag cat ctc aag gtt gga aag tat gag          725
Thr Asp Phe Ile Trp Pro Leu Lys His Leu Lys Val Gly Lys Tyr Glu
215                 220                 225                 230 aag agg atc gac gac atc ttg aac aag ttc gac cct gtc gtt gaa agg          773
Lys Arg Ile Asp Asp Ile Leu Asn Lys Phe Asp Pro Val Val Glu Arg
                235                 240                 245 gtc atc aag aag cgc cgt gag atc gtg agg agg aga aag aac gga gag          821
Val Ile Lys Lys Arg Arg Glu Ile Val Arg Arg Arg Lys Asn Gly Glu
            250                 255                 260 gtt gtt gag ggt gag gtc agc ggg gtt ttc ctt gac act ttg ctt gaa          869
Val Val Glu Gly Glu Val Ser Gly Val Phe Leu Asp Thr Leu Leu Glu
        265                 270                 275 ttc gct gag gat gag acc atg gag atc aaa atc acc aag gac cac atc          917
Phe Ala Glu Asp Glu Thr Met Glu Ile Lys Ile Thr Lys Asp His Ile
    280                 285                 290 aag ggt ctt gtt gtc gac ttt ttc tcg gca gga aca gac tcc aca gcg          965
```

| | | | | | | | | | | | | |
|---|---|---|---|---|---|---|---|---|---|---|---|---|
| Lys | Gly | Leu | Val | Val | Asp | Phe | Phe | Ser | Ala | Gly | Thr | Asp | Ser | Thr | Ala |
| 295 | | | | 300 | | | | 305 | | | | 310 |

```
gtg gca aca gag tgg gca ttg gca gaa ctc atc aac aat cct aag gtg      1013
Val Ala Thr Glu Trp Ala Leu Ala Glu Leu Ile Asn Asn Pro Lys Val
            315                 320                 325 ttg gaa aag gct cgt gag gag gtc tac agt gtt gtg gga aag gac aga      1061
Leu Glu Lys Ala Arg Glu Glu Val Tyr Ser Val Val Gly Lys Asp Arg
    330                 335                 340 ctt gtg gac gaa gtt gac act caa aac ctt cct tac att aga gca atc      1109
Leu Val Asp Glu Val Asp Thr Gln Asn Leu Pro Tyr Ile Arg Ala Ile
345                 350                 355 gtg aag gag aca ttc cgc atg cac ccg cca ctc cca gtg gtc aaa aga      1157
Val Lys Glu Thr Phe Arg Met His Pro Pro Leu Pro Val Val Lys Arg
        360                 365                 370 aag tgc aca gaa gag tgt gag att aat gga tat gtg atc cca gag gga      1205
Lys Cys Thr Glu Glu Cys Glu Ile Asn Gly Tyr Val Ile Pro Glu Gly
375                 380                 385                 390 gca ttg att ctc ttc aat gta tgg caa gta gga aga gac ccc aaa tac      1253
Ala Leu Ile Leu Phe Asn Val Trp Gln Val Gly Arg Asp Pro Lys Tyr
            395                 400                 405 tgg gac aga cca tcg gag ttc cgt cct gag agg ttc cta gag aca ggg      1301
Trp Asp Arg Pro Ser Glu Phe Arg Pro Glu Arg Phe Leu Glu Thr Gly
        410                 415                 420 gct gaa ggg gaa gca ggg cct ctt gat ctt agg gga caa cat ttt caa      1349
Ala Glu Gly Glu Ala Gly Pro Leu Asp Leu Arg Gly Gln His Phe Gln
    425                 430                 435 ctt ctc cca ttt ggg tct ggg agg aga atg tgc cct gga gtc aat ctg      1397
Leu Leu Pro Phe Gly Ser Gly Arg Arg Met Cys Pro Gly Val Asn Leu
440                 445                 450 gct act tcg gga atg gca aca ctt ctt gca tct ctt att cag tgc ttc      1445
Ala Thr Ser Gly Met Ala Thr Leu Leu Ala Ser Leu Ile Gln Cys Phe
455                 460                 465                 470 gac ttg caa gtg ctg ggt cca caa gga cag ata ttg aag ggt ggt gac      1493
Asp Leu Gln Val Leu Gly Pro Gln Gly Gln Ile Leu Lys Gly Gly Asp
            475                 480                 485 gcc aaa gtt agc atg gaa gag aga gcc ggc ctc act gtt cca agg gca      1541
Ala Lys Val Ser Met Glu Glu Arg Ala Gly Leu Thr Val Pro Arg Ala
        490                 495                 500 cat agt ctt gtc tgt gtt cca ctt gca agg atc ggc gtt gca tct aaa      1589
His Ser Leu Val Cys Val Pro Leu Ala Arg Ile Gly Val Ala Ser Lys
    505                 510                 515 ctc ctt tct taattaagat catcgtcatc atcatcatat gtaatattta              1638
Leu Leu Ser
        520 cttttttgtgt gttgataatc atcatttcaa taaggtctca ttcatctact ttttatgaag   1698
tatataagcc cttccatgc                                                 1717

<210> SEQ ID NO 2
<211> LENGTH: 521
<212> TYPE: PRT
<213> ORGANISM: Glycine max

<400> SEQUENCE: 2

Met Leu Leu Glu Leu Ala Leu Gly Leu Leu Val Leu Ala Leu Phe Leu
1               5                   10                  15

His Leu Arg Pro Thr Pro Thr Ala Lys Ser Lys Ala Leu Arg His Leu
            20                  25                  30

Pro Asn Pro Pro Ser Pro Lys Pro Arg Leu Pro Phe Ile Gly His Leu
        35                  40                  45
```

```
His Leu Leu Lys Asp Lys Leu His Tyr Ala Leu Ile Asp Leu Ser
     50                  55                  60

Lys Lys His Gly Pro Leu Phe Ser Leu Tyr Phe Gly Ser Met Pro Thr
 65                  70                  75                  80

Val Val Ala Ser Thr Pro Glu Leu Phe Lys Leu Phe Leu Gln Thr His
                 85                  90                  95

Glu Ala Thr Ser Phe Asn Thr Arg Phe Gln Thr Ser Ala Ile Arg Arg
            100                 105                 110

Leu Thr Tyr Asp Ser Ser Val Ala Met Val Pro Phe Gly Pro Tyr Trp
            115                 120                 125

Lys Phe Val Arg Lys Leu Ile Met Asn Asp Leu Leu Asn Ala Thr Thr
130                 135                 140

Val Asn Lys Leu Arg Pro Leu Arg Thr Gln Ile Arg Lys Phe Leu
145                 150                 155                 160

Arg Val Met Ala Gln Gly Ala Glu Ala Gln Lys Pro Leu Asp Leu Thr
                165                 170                 175

Glu Glu Leu Leu Lys Trp Thr Asn Ser Thr Ile Ser Met Met Met Leu
            180                 185                 190

Gly Glu Ala Glu Glu Ile Arg Asp Ile Ala Arg Glu Val Leu Lys Ile
            195                 200                 205

Phe Gly Glu Tyr Ser Leu Thr Asp Phe Ile Trp Pro Leu Lys His Leu
210                 215                 220

Lys Val Gly Lys Tyr Glu Lys Arg Ile Asp Asp Ile Leu Asn Lys Phe
225                 230                 235                 240

Asp Pro Val Val Glu Arg Val Ile Lys Lys Arg Arg Glu Ile Val Arg
                245                 250                 255

Arg Arg Lys Asn Gly Glu Val Val Glu Gly Glu Val Ser Gly Val Phe
            260                 265                 270

Leu Asp Thr Leu Leu Glu Phe Ala Glu Asp Thr Met Glu Ile Lys
            275                 280                 285

Ile Thr Lys Asp His Ile Lys Gly Leu Val Val Asp Phe Phe Ser Ala
290                 295                 300

Gly Thr Asp Ser Thr Ala Val Ala Thr Glu Trp Ala Leu Ala Glu Leu
305                 310                 315                 320

Ile Asn Asn Pro Lys Val Leu Glu Lys Ala Arg Glu Glu Val Tyr Ser
                325                 330                 335

Val Val Gly Lys Asp Arg Leu Val Asp Glu Val Asp Thr Gln Asn Leu
            340                 345                 350

Pro Tyr Ile Arg Ala Ile Val Lys Glu Thr Phe Arg Met His Pro Pro
            355                 360                 365

Leu Pro Val Val Lys Arg Lys Cys Thr Glu Glu Cys Glu Ile Asn Gly
            370                 375                 380

Tyr Val Ile Pro Glu Gly Ala Leu Ile Leu Phe Asn Val Trp Gln Val
385                 390                 395                 400

Gly Arg Asp Pro Lys Tyr Trp Asp Arg Pro Ser Glu Phe Arg Pro Glu
                405                 410                 415

Arg Phe Leu Glu Thr Gly Ala Glu Gly Glu Ala Gly Pro Leu Asp Leu
            420                 425                 430

Arg Gly Gln His Phe Gln Leu Leu Pro Phe Gly Ser Gly Arg Arg Met
            435                 440                 445

Cys Pro Gly Val Asn Leu Ala Thr Ser Gly Met Ala Thr Leu Leu Ala
450                 455                 460
```

```
Ser Leu Ile Gln Cys Phe Asp Leu Gln Val Leu Gly Pro Gln Gly Gln
465                 470                 475                 480

Ile Leu Lys Gly Gly Asp Ala Lys Val Ser Met Glu Glu Arg Ala Gly
                485                 490                 495

Leu Thr Val Pro Arg Ala His Ser Leu Val Cys Val Pro Leu Ala Arg
                500                 505                 510

Ile Gly Val Ala Ser Lys Leu Leu Ser
            515                 520

<210> SEQ ID NO 3
<211> LENGTH: 523
<212> TYPE: PRT
<213> ORGANISM: Glycyrrhiza echinata

<400> SEQUENCE: 3

Met Glu Pro Gln Leu Val Ala Val Ser Val Leu Val Ser Ala Leu Ile
1               5                   10                  15

Cys Tyr Phe Phe Arg Pro Tyr Phe His Arg Tyr Gly Lys Asn Leu
            20                  25                  30

Pro Pro Ser Pro Phe Arg Leu Pro Ile Ile Gly His Met His Met
            35                  40                  45

Leu Gly Pro Leu His Gln Ser Phe His Asn Leu Ser His Arg Tyr
        50                  55                  60

Gly Pro Leu Phe Ser Leu Asn Phe Gly Ser Val Leu Cys Val Val Ala
65                  70                  75                  80

Ser Thr Pro His Phe Ala Lys Gln Leu Leu Gln Thr Asn Glu Leu Ala
                85                  90                  95

Phe Asn Cys Arg Ile Glu Ser Thr Ala Val Lys Lys Leu Thr Tyr Glu
                100                 105                 110

Ser Ser Leu Ala Phe Ala Pro Tyr Gly Asp Tyr Trp Arg Phe Ile Lys
            115                 120                 125

Lys Leu Ser Met Asn Glu Leu Leu Gly Ser Arg Ser Ile Asn Asn Phe
            130                 135                 140

Gln His Leu Arg Ala Gln Glu Thr His Gln Leu Leu Arg Leu Leu Ser
145                 150                 155                 160

Asn Arg Ala Arg Ala Phe Glu Ala Val Asn Ile Thr Glu Glu Leu Leu
                165                 170                 175

Lys Leu Thr Asn Asn Val Ile Ser Ile Met Met Val Gly Glu Ala Glu
            180                 185                 190

Glu Ala Arg Asp Val Val Arg Asp Val Thr Glu Ile Phe Gly Glu Phe
            195                 200                 205

Asn Val Ser Asp Phe Ile Trp Leu Phe Lys Lys Met Asp Leu Gln Gly
210                 215                 220

Phe Gly Lys Arg Ile Glu Asp Leu Phe Gln Arg Phe Asp Thr Leu Val
225                 230                 235                 240

Glu Arg Ile Ile Ser Lys Arg Glu Gln Thr Arg Lys Asp Arg Arg Arg
                245                 250                 255

Asn Gly Lys Lys Gly Glu Gln Gly Ser Gly Asp Gly Ile Arg Asp Phe
            260                 265                 270

Leu Asp Ile Leu Leu Asp Cys Thr Glu Asp Glu Asn Ser Glu Ile Lys
            275                 280                 285

Ile Gln Arg Val His Ile Lys Ala Leu Ile Met Asp Phe Phe Thr Ala
290                 295                 300

Gly Thr Asp Thr Thr Ala Ile Ser Thr Glu Trp Ala Leu Val Glu Leu
305                 310                 315                 320
```

```
Val Lys Lys Pro Ser Val Leu Gln Lys Val Arg Glu Ile Asp Asn
            325                 330                 335

Val Val Gly Lys Asp Arg Leu Val Glu Glu Ser Asp Cys Pro Asn Leu
            340                 345                 350

Pro Tyr Leu Gln Ala Ile Leu Lys Glu Thr Phe Arg Leu His Pro Pro
            355                 360                 365

Val Pro Met Val Thr Arg Arg Cys Val Ala Glu Cys Thr Val Glu Asn
        370                 375                 380

Tyr Val Ile Pro Glu Asp Ser Leu Leu Phe Val Asn Val Trp Ser Ile
385                 390                 395                 400

Gly Arg Asn Pro Lys Phe Trp Asp Asn Pro Leu Glu Phe Arg Pro Glu
                405                 410                 415

Arg Phe Leu Lys Leu Glu Gly Asp Ser Ser Gly Val Val Asp Val Arg
                420                 425                 430

Gly Ser His Phe Gln Leu Leu Pro Phe Gly Ser Gly Arg Arg Met Cys
            435                 440                 445

Pro Gly Val Ser Leu Ala Met Gln Glu Val Pro Ala Leu Leu Gly Ala
        450                 455                 460

Ile Ile Gln Cys Phe Asp Phe His Val Val Gly Pro Lys Gly Glu Ile
465                 470                 475                 480

Leu Lys Gly Asp Asp Ile Val Ile Asn Val Asp Glu Arg Pro Gly Leu
                485                 490                 495

Thr Ala Pro Arg Ala His Asn Leu Val Cys Val Pro Val Asp Arg Thr
            500                 505                 510

Ser Gly Gly Gly Pro Leu Lys Ile Ile Glu Cys
        515                 520

<210> SEQ ID NO 4
<211> LENGTH: 1811
<212> TYPE: DNA
<213> ORGANISM: Medicago truncatula
<220> FEATURE:
<221> NAME/KEY: CDS
<222> LOCATION: (92)..(1657)

<400> SEQUENCE: 4
caacacctaa gagtaactaa taagaacttt ctttctactt cttagtatac ttaacaactt      60
aagtaaatat actacaaaga agctatacac c atg ttg gtg gaa ctt gca gtt      112
                                  Met Leu Val Glu Leu Ala Val
                                    1               5 act cta ttg ctc att gct ctc ttc tta cac ttg cgt cca aca cct act      160
Thr Leu Leu Leu Ile Ala Leu Phe Leu His Leu Arg Pro Thr Pro Thr
         10                  15                  20 gca aaa tca aag gct ctt cgc cac ctt cca aat cca cca agc cct aaa      208
Ala Lys Ser Lys Ala Leu Arg His Leu Pro Asn Pro Pro Ser Pro Lys
 25                  30                  35 cca cgt ctt cca ttc ata ggt cat ctt cac ctt ttg gat aac cca ctt      256
Pro Arg Leu Pro Phe Ile Gly His Leu His Leu Leu Asp Asn Pro Leu
 40                  45                  50                  55 ctt cac cac act ctt atc aag tta gga aag cgt tat ggc cct ttg tac      304
Leu His His Thr Leu Ile Lys Leu Gly Lys Arg Tyr Gly Pro Leu Tyr
             60                  65                  70 act ctt tac ttt ggt tcc atg cct acc gtt gtt gca tcc act cct gac      352
Thr Leu Tyr Phe Gly Ser Met Pro Thr Val Val Ala Ser Thr Pro Asp
         75                  80                  85 ttg ttt aaa ctt ttc ctt caa acc cat gaa gct act tcc ttt aac aca      400
Leu Phe Lys Leu Phe Leu Gln Thr His Glu Ala Thr Ser Phe Asn Thr
```

```
                     90                  95                 100
aga ttc caa acc tct gct att agt cgt ctt acc tat gac aac tct gtt       448
Arg Phe Gln Thr Ser Ala Ile Ser Arg Leu Thr Tyr Asp Asn Ser Val
        105                 110                 115 gct atg gtt cca ttt gca cct tat tgg aag ttt att aga aag ctt atc       496
Ala Met Val Pro Phe Ala Pro Tyr Trp Lys Phe Ile Arg Lys Leu Ile
120                 125                 130                 135 atg aac gac ttg ctc aac gcc acc act gtt aac aaa ttg agg cca ttg       544
Met Asn Asp Leu Leu Asn Ala Thr Thr Val Asn Lys Leu Arg Pro Leu
                140                 145                 150 agg agc cga gaa atc ctt aag gtt ctt aag gtc atg gct aat agt gct       592
Arg Ser Arg Glu Ile Leu Lys Val Leu Lys Val Met Ala Asn Ser Ala
        155                 160                 165 gaa act caa cag cca ctt gat gtc act gag gag ctt ctc aag tgg aca       640
Glu Thr Gln Gln Pro Leu Asp Val Thr Glu Glu Leu Leu Lys Trp Thr
170                 175                 180 aac agc aca atc tct acc atg atg ttg ggt gag gcc gaa gag gtt aga       688
Asn Ser Thr Ile Ser Thr Met Met Leu Gly Glu Ala Glu Glu Val Arg
        185                 190                 195 gat att gct cgt gat gtt ctt aag atc ttt gga gaa tat agt gtt aca       736
Asp Ile Ala Arg Asp Val Leu Lys Ile Phe Gly Glu Tyr Ser Val Thr
200                 205                 210                 215 aac ttt att tgg cct ttg aac aag ttt aag ttt gga aac tat gat aag       784
Asn Phe Ile Trp Pro Leu Asn Lys Phe Lys Phe Gly Asn Tyr Asp Lys
                220                 225                 230 aga act gag gag att ttc aat aag tat gat cct atc att gaa aag gtt       832
Arg Thr Glu Glu Ile Phe Asn Lys Tyr Asp Pro Ile Ile Glu Lys Val
        235                 240                 245 atc aag aaa cga caa gag att gtg aac aaa aga aaa aat gga gaa atc       880
Ile Lys Lys Arg Gln Glu Ile Val Asn Lys Arg Lys Asn Gly Glu Ile
                250                 255                 260 gta gaa ggc gag cag aat gtt gtt ttt ctt gac act ttg ctt gaa ttt       928
Val Glu Gly Glu Gln Asn Val Val Phe Leu Asp Thr Leu Leu Glu Phe
        265                 270                 275 gca caa gat gag acc atg gag atc aaa att aca aag gaa caa atc aag       976
Ala Gln Asp Glu Thr Met Glu Ile Lys Ile Thr Lys Glu Gln Ile Lys
280                 285                 290                 295 ggt ctt gtt gtg gat ttt ttc tct gca gga aca gac tcc acc gcc gtg      1024
Gly Leu Val Val Asp Phe Phe Ser Ala Gly Thr Asp Ser Thr Ala Val
                300                 305                 310 tct aca gaa tgg act tta tca gag ctc atc aat aat cct aga gtg ttg      1072
Ser Thr Glu Trp Thr Leu Ser Glu Leu Ile Asn Asn Pro Arg Val Leu
        315                 320                 325 aag aaa gct cga gag gag att gac tct gtt gtg gga aaa gat aga ctg      1120
Lys Lys Ala Arg Glu Glu Ile Asp Ser Val Val Gly Lys Asp Arg Leu
                330                 335                 340 gtt gat gaa tca gat gtt cag aat ctt cct tac att aaa gcc atc gta      1168
Val Asp Glu Ser Asp Val Gln Asn Leu Pro Tyr Ile Lys Ala Ile Val
345                 350                 355 aaa gaa gca ttt cgc ttg cac cca cca cta cct gta gtc aaa aga aaa      1216
Lys Glu Ala Phe Arg Leu His Pro Pro Leu Pro Val Val Lys Arg Lys
360                 365                 370                 375 tgt aca caa gaa tgt gag atc gac ggg tat gtg gtt cca gaa gga gca      1264
Cys Thr Gln Glu Cys Glu Ile Asp Gly Tyr Val Val Pro Glu Gly Ala
                380                 385                 390 cta ata ctt ttc aat gtc tgg gca gtg gga aga gac cca aaa tat tgg      1312
Leu Ile Leu Phe Asn Val Trp Ala Val Gly Arg Asp Pro Lys Tyr Trp
        395                 400                 405 gta aag cca ttg gaa ttt cgt cca gag agg ttc ata gaa aat gtt ggt      1360
Val Lys Pro Leu Glu Phe Arg Pro Glu Arg Phe Ile Glu Asn Val Gly
```

```
                 Val Lys Pro Leu Glu Phe Arg Pro Glu Arg Phe Ile Glu Asn Val Gly
                     410                 415                 420 gaa ggt gaa gca gct tca att gat ctt agg ggt caa cat ttc aca ctt     1408
Glu Gly Glu Ala Ala Ser Ile Asp Leu Arg Gly Gln His Phe Thr Leu
    425                 430                 435 cta cca ttt ggg tct gga aga agg atg tgt cct gga gtc aat ttg gct     1456
Leu Pro Phe Gly Ser Gly Arg Arg Met Cys Pro Gly Val Asn Leu Ala
440                 445                 450                 455 act gca gga atg gcc aca atg att gca tct att atc caa tgc ttc gat     1504
Thr Ala Gly Met Ala Thr Met Ile Ala Ser Ile Ile Gln Cys Phe Asp
                460                 465                 470 ctc caa gta cct ggt caa cat gga gaa ata ttg aat ggt gat tat gct     1552
Leu Gln Val Pro Gly Gln His Gly Glu Ile Leu Asn Gly Asp Tyr Ala
            475                 480                 485 aag gtt agc atg gaa gag aga cct ggt ctc aca gtt cca agg gca cat     1600
Lys Val Ser Met Glu Glu Arg Pro Gly Leu Thr Val Pro Arg Ala His
        490                 495                 500 aat ctc atg tgt gtt cct ctt gca aga gct ggt gtc gca gat aaa ctt     1648
Asn Leu Met Cys Val Pro Leu Ala Arg Ala Gly Val Ala Asp Lys Leu
    505                 510                 515 ctt tcc tcc taaaatatct tgagaggatg aatcaccaac atatagcctc             1697
Leu Ser Ser
520 tctttggtac tacaaaatta tgatgtaatt ttcttatttt ttctgtcaca aaggaagtgt   1757 tgtaacttgt aattgcatac aaaatctata aattttatca tcctattcat tatt         1811

<210> SEQ ID NO 5
<211> LENGTH: 522
<212> TYPE: PRT
<213> ORGANISM: Medicago truncatula

<400> SEQUENCE: 5

Met Leu Val Glu Leu Ala Val Thr Leu Leu Ile Ala Leu Phe Leu
 1               5                  10                  15

His Leu Arg Pro Thr Pro Thr Ala Lys Ser Lys Ala Leu Arg His Leu
                20                  25                  30

Pro Asn Pro Pro Ser Pro Lys Pro Arg Leu Pro Phe Ile Gly His Leu
            35                  40                  45

His Leu Leu Asp Asn Pro Leu His His Thr Leu Ile Lys Leu Gly
        50                  55                  60

Lys Arg Tyr Gly Pro Leu Tyr Thr Leu Tyr Phe Gly Ser Met Pro Thr
65                  70                  75                  80

Val Val Ala Ser Thr Pro Asp Leu Phe Lys Leu Phe Leu Gln Thr His
                85                  90                  95

Glu Ala Thr Ser Phe Asn Thr Arg Phe Gln Thr Ser Ala Ile Ser Arg
            100                 105                 110

Leu Thr Tyr Asp Asn Ser Val Ala Met Val Pro Phe Ala Pro Tyr Trp
        115                 120                 125

Lys Phe Ile Arg Lys Leu Ile Met Asn Asp Leu Leu Asn Ala Thr Thr
    130                 135                 140

Val Asn Lys Leu Arg Pro Leu Arg Ser Arg Glu Ile Leu Lys Val Leu
145                 150                 155                 160

Lys Val Met Ala Asn Ser Ala Glu Thr Gln Gln Pro Leu Asp Val Thr
                165                 170                 175

Glu Glu Leu Leu Lys Trp Thr Asn Ser Thr Ile Ser Thr Met Met Leu
            180                 185                 190
```

-continued

```
Gly Glu Ala Glu Glu Val Arg Asp Ile Ala Arg Asp Val Leu Lys Ile
            195                 200                 205

Phe Gly Glu Tyr Ser Val Thr Asn Phe Ile Trp Pro Leu Asn Lys Phe
            210                 215                 220

Lys Phe Gly Asn Tyr Asp Lys Arg Thr Glu Glu Ile Phe Asn Lys Tyr
225                 230                 235                 240

Asp Pro Ile Ile Glu Lys Val Ile Lys Lys Arg Gln Glu Ile Val Asn
                245                 250                 255

Lys Arg Lys Asn Gly Glu Ile Val Glu Gly Glu Gln Asn Val Val Phe
                260                 265                 270

Leu Asp Thr Leu Leu Glu Phe Ala Gln Asp Glu Thr Met Glu Ile Lys
            275                 280                 285

Ile Thr Lys Glu Gln Ile Lys Gly Leu Val Val Asp Phe Phe Ser Ala
            290                 295                 300

Gly Thr Asp Ser Thr Ala Val Ser Thr Glu Trp Thr Leu Ser Glu Leu
305                 310                 315                 320

Ile Asn Asn Pro Arg Val Leu Lys Lys Ala Arg Glu Glu Ile Asp Ser
                325                 330                 335

Val Val Gly Lys Asp Arg Leu Val Asp Glu Ser Asp Val Gln Asn Leu
                340                 345                 350

Pro Tyr Ile Lys Ala Ile Val Lys Glu Ala Phe Arg Leu His Pro Pro
            355                 360                 365

Leu Pro Val Val Lys Arg Lys Cys Thr Gln Glu Cys Glu Ile Asp Gly
            370                 375                 380

Tyr Val Val Pro Glu Gly Ala Leu Ile Leu Phe Asn Val Trp Ala Val
385                 390                 395                 400

Gly Arg Asp Pro Lys Tyr Trp Val Lys Pro Leu Glu Phe Arg Pro Glu
                405                 410                 415

Arg Phe Ile Glu Asn Val Gly Glu Gly Glu Ala Ala Ser Ile Asp Leu
            420                 425                 430

Arg Gly Gln His Phe Thr Leu Leu Pro Phe Gly Ser Gly Arg Arg Met
            435                 440                 445

Cys Pro Gly Val Asn Leu Ala Thr Ala Gly Met Ala Thr Met Ile Ala
            450                 455                 460

Ser Ile Ile Gln Cys Phe Asp Leu Gln Val Pro Gly Gln His Gly Glu
465                 470                 475                 480

Ile Leu Asn Gly Asp Tyr Ala Lys Val Ser Met Glu Glu Arg Pro Gly
                485                 490                 495

Leu Thr Val Pro Arg Ala His Asn Leu Met Cys Val Pro Leu Ala Arg
            500                 505                 510

Ala Gly Val Ala Asp Lys Leu Leu Ser Ser
            515                 520
```

GENETIC MANIPULATION OF ISOFLAVONOIDS

PRIORITY INFORMATION

This application is a §371 filing of International Application No. PCT/US00/05915, filed on Mar. 8, 2000, which claims benefit of Provisional Application No. 60/123,267, filed Mar. 8, 1999.

TECHNICAL FIELD OF THE INVENTION

The invention relates to gene manipulation in plants.

BACKGROUND OF THE INVENTION

The flavonoids are a major class of phenylpropanoid-derived plant natural products. Their fifteen carbon ($C_6$–$C_3$–$C_6$) backbone can be arranged as a 1,3-diphenylpropane skeleton (flavonoid nucleus) or as a 1,2-diphenylpropane skeleton (isoflavonoid nucleus). Although 1,3-diphenylpropane flavonoid derivatives are almost ubiquitous among terrestrial plants, the 1,2-diphenylpropane isoflavonoids are restricted primarily to the Leguminosae, although they occur rarely in other families such as the Apocynaceae, Pinaceae, Compositae, and Moraceae (Tahara, S. and R. K. Ibrahim, 1995, "Prenylated isoflavonoids—an update," *Phytochemistry* 38: 1073–1094).

The limited taxonomic distribution of the isoflavonoids is directly related to the occurrence of the enzyme complex isoflavone synthase (IFS), which catalyzes the aryl migration reaction leading to the formation of an isoflavone from a flavanone. While flavanones are ubiquitous in higher plants, the IFS reaction, which is a two-step process specific for isoflavonoid biosynthesis (Kochs, G. and H. Grisebach, 1986, "Enzymic synthesis of isoflavones," *European J Biochem* 155: 311–318), is limited to the Leguminosae and the other diverse taxa in which isoflavonoids are occasionally found.

The presence of isoflavonoids provides several advantages to plants. One such advantage is provided by the function of isoflavonoids as antimicrobial phytoalexins in plant-microbe interactions. For example, the simple isoflavones daidzein and genistein act as initial precursors in the biosynthesis of various antimicrobial isoflavonoid phytoalexins in a wide variety of legumes (Dixon, R. A. and N. L. Paiva, 1995, "Stress-induced phenylpropanoid metabolism," *Plant Cell* 7: 1085–1097). Isoflavonoid compounds have been shown to accumulate in infected plant cells to levels known to be antimicrobial in vitro. The temporal, spatial and quantitative aspects of accumulation are consistent with a role for these compounds in disease resistance (Rahe, J. E., 1973, "Occurrence and levels of the phytoalexin phaseollin in relation to delimitation at sites of infection of *Phaseolus vulgaris* by *Colletotrichum lindemuthianum*," *Canadian J Botany* 51: 2423–2430; Hadwiger, L. A. and D. M. Webster, 1984, "Phytoalexin production in five cultivars of pea differentially resistant to three races of *Pseudomonas syringae* pv. *pisi*," *Phytopathology* 74: 1312–1314; Long, et al., 1985, "Further studies on the relationship between glyceollin accumulation and the resistance of soybean leaves to *Pseudomonas syringae* pv. *glycinea*," *Phytopathology* 75: 235–239; Bhattacharyya, M. K. and E. W. B. Ward, 1987, "Biosynthesis and metabolism of glyceollin I in soybean hypocotyls following wounding or inoculation with *Phytophthora megasperma* f. sp. *glycinea*," *Physiol and Mol Plant Pathology* 31: 387–405). Moreover, it has been reported that many plant pathogens are much more sensitive to phytoalexins of non-host species than they are to the phytoalexins of their natural hosts, because they can often detoxify the host's phytoalexins. (VanEtten, et al., 1989, "Phytoalexin detoxification: importance for pathogenicity and practical implications," *An Rev Phytopathology* 27: 143–164).

Isoflavonoids also function in plant-microbe interactions in the establishment of bacterial or fungal symbioses with plants. Isoflavonoids have been reported to regulate bacterial nodulation genes, acting as a major nod gene inducer (Kosslak, et al., 1987, "Induction of *Bradyrhizobium japonicum* common nod genes by isoflavones isolated from *Glycine max*," *Proc Natl Acad Sci USA* 84: 7428–7432) and/or transcription activator (Dakora, et al., 1993, "Common bean root exudates contain elevated levels of daidzein and coumestrol in response to *Rhizobium* inoculation," *Mol Plant-Microbe Interact* 6: 665–668). Isoflavonoids have also been shown to have a role on the establishment of the symbiotic vesicular arbuscular mycorrhizal (VAM) association of the fungus *Glomus* with legume roots. (Kape, et al., 1992, "Legume root metabolites and VA-mycorrhiza development," *J Plant Physiol* 141: 54–60). Xie et al have reported that the isoflavonoids coumestrol, daidzein and genistein have small but significant stimulatory effects on the degree of mycorrhizal colonization of soybean, and that one effect of isoflavonoids on the soybean mycorrhizal symbiosis could be via induction of nodulation factors from co-colonizing *Rhizobia*, since nod-factors have also been shown to stimulate fungal colonization (Xie, et al., 1995, "Rhizobial nodulation factors stimulate mycorrhizal colonization of nodulating and nonnodulating soybeans," *Plant Physiology* 108: 1519–1525).

In addition to the advantages that the presence of isoflavonoids confers to plants, a significant body of evidence indicates that dietary consumption of isoflavonoids can provide benefits to human health. Dietary isoflavones have been ascribed strong cancer chemopreventative activity in humans, and display a range of pharmacological activities suggestive of various other health promoting effects, including phytoestrogen activity as both estrogenic and anti-estrogenic agents (Coward, et al., 1993, "Genistein, daidzein, and their -glycoside conjugates: antitumor isoflavones in soybean foods from American and Asian diets," *J Agricultural and Food Chemistry* 41: 1961–1967; Martin, et al., 1996, "Interactions between phytoestrogens and human sex steroid binding protein," *Life Sciences* 58: 429–436); anticancer effects associated with phytoestrogenic activity (Lee, et al., 1991, "Dietary effects on breast-cancer risk in Singapore," *Lancet* 337: 1197–1200; Adlercreutz, et al., 1991, "Urinary excretion of lignans and isoflavonoid phytoestrogens in Japanese men and women consuming a traditional Japanese diet," *Am J Clin Nutr* 54: 1093–1100); anticancer effects associated with inhibition of several enzymes including DNA topoisomerase and tyrosine protein kinase (Akiyama, et al., 1987, "Genistein, a specific inhibitor of tyrosine-specific protein kinases," *J Biol Chem* 262: 5592–559; Uckun, et al., 1995, "Biotherapy of B-cell precursor leukemia by targeting genistein to CD19-associated tyrosine kinases," *Science* 267: 886–891); suppression of alcohol consumption (Keung, W. M. and B. L. Vallee, 1993, "Daidzin: A potent, selective inhibitor of human mitochondrial aldehyde dehydrogenase," *Proc Natl Acad Sci USA* 90: 1247–1251; Keung, et al., 1995, "Daidzin suppresses ethanol consumption by Syrian golden hamsters without blocking acetaldehyde metabolism," *Proc Natl Acad Sci USA* 92: 8990–8993); antioxidant activity (Arora, et al., 1998, "Antioxidant activities of isoflavones and their biological metabolites in a lipsomal system," *Arch Biochem Biophys* 356: 133–141; Tikkanen, et al., 1998, "Effect of soybean phytoestrogen intake on low density lipoprotein oxidation resistance," *Proc Natl Acad Sci USA* 95: 3106–3110); effects on calcium metabolism, some of which may be linked to protective effects against osteoporosis (Tomonaga, et al., 1992, "Isoflavonoids, genistein, PSI-tectorigenin, and orobol, increase cytoplasmic free calcium in isolated rat hepatocytes," *Biochem Biophys Res Com* 182: 894–899; Draper, et al., 1997, "Phytoestrogens reduce bone loss and bone resorption in oophorectomized rats," *J Nutr* 127: 1795–1799); and cardiovascular effects (Wagner, et al., 1997, "Dietary soy protein and estrogen replacement therapy improve cardiovascular risk factors and decrease aortic cholesteryl ester content in ovariectomized cynomolgus monkeys," *Metabolism—Clinical and Experimental* 46: 698–705).

At present, the only dietary sources of isoflavonoids for humans are certain legumes such as soybean or chickpea. The development of methods to genetically manipulate isoflavonoids in plants, either to widen the source of dietary isoflavonoids for humans, or to exploit the biological activities of isoflavonoids for plant protection and improvement, is wholly dependent on the availability of cloned genes encoding the various enzymes of isoflavonoid biosynthesis. Of these, the isoflavone synthase (IFS) complex constitutes the first committed reactions, and as such represents the means to introduce isoflavonoids into plants that do not possess the pathway.

In 1984, Hagmann and Grisebach provided the first evidence for the enzymatic conversion of flavanone to isoflavone (the IFS reaction) in a cell free system (Hagmann, M. and H. Grisebach, 1984, "Enzymatic rearrangement of flavanone to isoflavone," FEBS Letters 175: 199–202). They demonstrated that microsomes from elicitor-treated soybean cell suspension cultures could catalyze the conversion of 2(S)-naringenin to genistein, or of 2(S)-liquiritigenin to daidzein, in the presence of NADPH. The crude microsomal enzyme preparation, which was stable at −70° C. but had a half-life of only 10 minutes at room temperature, was absolutely dependent on NADPH and molecular oxygen. It was subsequently shown that the reaction proceeded in two steps. The flavanone was converted in a cytochrome P450-catalyzed reaction requiring NADPH and $O_2$ to the corresponding 2-hydroxyisoflavanone. This relatively unstable compound, which could, however, be identified by mass spectrometric analysis, then underwent dehydration to yield the isoflavone. The dehydration reaction appeared to be catalyzed by an enzyme present predominantly in the cytoplasmic supernatant, although it was not possible to remove all this activity from the microsomes. The corresponding 2-hydroxyisoflavanone spontaneously converted to genistein, for example, in methanol at room temperature. Kinetic analysis indicated that the 2-hydroxyisoflavanone was formed prior to genistein, consistent with its being an intermediate in isoflavone formation. (Kochs, G. and H. Grisebach, 1986, "Enzymic synthesis of isoflavones," *European J Biochem* 155: 311–318).

Involvement of cytochrome P450 in the 2-hydroxyisoflavanone synthase reaction was confirmed by inhibition by CO, replacing $O_2$ with $N_2$, and examining the effects of a range of known P450 inhibitors of which ancymidol was the most effective. The enzyme co-migrated with the endoplasmic reticulum markers cinnamic 4-hydroxylase (another cytochrome P450) and cytochrome b5 reductase on Percoll gradients. The enzyme is stereoselective, and (2R)-naringenin is not a substrate. (Kochs, G. and H. Grisebach, 1986, "Enzymic synthesis of isoflavones," *European J Biochem* 155: 311–318).

The origin of the 2-hydroxyl group was determined from studies on the IFS present in microsomes from elicited cell cultures of *Pueraria lobata*. $^{18}O$ from $^{18}O_2$ was incorporated into the 2-hydroxyl group, resulting in a 2-hydroxyisoflavanone with molecular ion shifted by two mass units, whereas there was no corresponding shift in the molecular ion of daidzein, consistent with the subsequent dehydration reaction (Hashim, et al., 1990, "Reaction mechanism of oxidative rearrangement of flavanone in isoflavone biosynthesis," *FEBS Letters* 271: 219–222). The currently accepted model for the reaction pathway of IFS as illustrated in FIG. 1, therefore, involves P450-catalyzed hydroxylation coupled to aryl migration, a reaction with mechanistic similarities to the well described proton migration mechanism of some P450 reactions (Hakamatsuka, et al., 1991, "P450-dependent oxidative rearrangement in isoflavone biosynthesis: reconstitution of P-450 and NADPH:P450 reductase," *Tetrahedron* 47: 5969–5978).

Currently, there have been no reports on purification to homogeneity or molecular cloning of the cytochrome P450 of the IFS complex because of the extreme lability of the enzyme. The 2-hydroxyisoflavanone synthase cytochrome P450 from Pueraria has been solubilized with Triton X-100, and partially purified by DEAE-Sepharose chromatography; the enzymatic reaction could be reconstituted by addition of NADPH cytochrome P450 reductase that separated from the hydroxylase on the ion exchange column (Hakamatsuka, et al., 1991, *Tetrahedron* 47: 5969–5978). A 2-hydroxyisoflavanone dehydratase has been purified from elicitor-treated *P. lobata* cells, and has been shown to be a soluble monomeric enzyme of subunit Mr 38,000 (Hakamatsuka, et al., 1998, "Purification of 2-hydroxyisoflavanone dehydratase from the cell cultures of *Pueraria lobata*," Phytochemistry 49: 497–505). It is not yet clear whether this enzyme physically associates with the P450 hydroxylase catalyzing the aryl migration, or even whether this activity is essential for isoflavone formation in planta in view of the spontaneous conversion of 2-hydroxyisoflavanone to isoflavone.

Flavanone is a potential substrate for more than one type of hydroxylation reaction at the 2-position. Thus, elicitor-treated cell cultures of alfalfa and *Glycyrrhiza echinata* have been shown to accumulate the dibenzoylmethane licodione (Kirikae, et al., 1993, "Biosynthesis of a dibenzoylmethane, licodione, in cultured alfalfa cells induced by yeast extract," *Biosci Biotech Biochem* 57: 1353–1354). Licodione synthase is, by classical criteria, a cytochrome P450, the activity of which is induced by yeast elicitor in *Glycyrrhiza* cells (Otani, et al., 1994, "Licodione synthase, a cytochrome P450 monooxygenase catalyzing 2-hydroxylation of 5-deoxyflavanone, in cultured *Glycyrrhiza echinata* L. cells," *Plant Physiol* 105: 1427–1432). The reaction it catalyzes involves 2-hydroxylation of flavanone followed by hemiacetal opening instead of aryl migration, and the reaction was thought to have mechanistic similarities to the flavone synthase II enzyme previously characterized from soybean (Kochs, G. and H. Grisebach, 1987, "Induction and characterization of a NADPH-dependent flavone synthase from cell cultures of soybean," *Z. Naturforsch* 42C: 343–348). A gene encoding the flavone synthase II/licodione synthase from *Glycyrrhiza* has been cloned (Akashi, et al., 1998, "Identification of a cytochrome P450 cDNA encoding (2S)-flavanone 2-hydroxylase of licorice (*Glycyrrhiza echinata* L.; *Fabaceae*) which represents licodione synthase and flavone synthase II," *FEBS Letters* 431: 287–290), and a different cytochrome P450 gene encoding flavone synthase II has recently been cloned from *Gerbera hybrida* (Martens, S. and G. Forkmann, "Cloning and expression of flavone synthase II from Gerbera hybrids," *Plant J* 20: 611–618).

Although the reactions catalyzed by IFS are critical for the formation of all isoflavonoids in plants, there have been no previous reports of the isolation of genes encoding components of isoflavone synthase, although genes encoding most of the other enzymes of the isoflavonoid pathway, including downstream enzymes converting simple isoflavones to antimicrobial phytoalexins, have been characterized (Dixon, et al., 1995, "The isoflavonoid phytoalexin pathway: from enzymes to genes to transcription factors," *Physiologia Plantarum* 93: 385–392). Thus, the unavailability of isoflavone synthase genes has made it heretofore impossible to utilize the downstream genes for regulating isoflavonoid concentrations in legumes and other plants that do have the isoflavonoid pathway, or for engineering antimicrobial and pharmacologically active isoflavonoids in transgenic plants of species that do not have the isoflavonoid pathway.

Genes encoding the enzyme catalyzing the first step of the isoflavone synthase reaction have now been isolated and purified from soybean and *Medicago truncatula* (barrel medic).

BRIEF DESCRIPTION OF THE DRAWINGS

FIG. 2 depicts the nucleotide sequence of soybean CYP93C1v2(SEQ ID NO:1).

FIG. 3 depicts the amino acid sequence of soybean CYP93v2 (SEQ ID NO:2) compared to licorice CYP93B1 (SEQ ID NO:3).

FIG. 4 depicts the nucleotide sequence of *Medicago truncatula* mtIFSE3 (SEQ ID NO:4).

FIG. 5 depicts the amino acid sequence of *Medicago truncatula* mtIFSE3 (SEQ ID NO:5) compared to soybean CYP93C1v2 (SEQ ID NO:2).

FIG. 8A depicts the presence of NADPH during incubation with liquiritigenin. FIG. 8B depicts the absence of NADPH during incubation with liquiritigenin. FIG. 8C depicts the presence of NADPH during incubation with naringenin. FIG. 8D depicts the lack of a reaction when soybean CYP93E expressed in insect cells is incubated with liquiritigenin in the presence of NADPH.

FIG. 9A depicts the mass spectrum of the BSTFA derivative of the product of the reaction catalyzed by CYP93C1v2 in insect cells using liquiritigenin as substrate, and FIG. 9B shows the mass spectrum of the BSTFA derivative of an authentic sample of daidzein.

SUMMARY OF THE INVENTION

Figure 1:
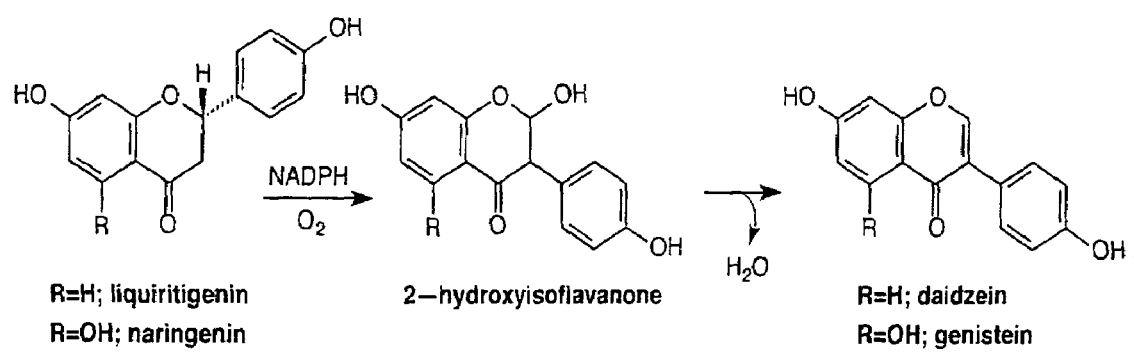
FIG. 1 depicts the currently accepted model for the reaction pathway of IFS wherein the flavanone is converted in a cytochrome P450-catalyzed reaction requiring NADPH and $O_2$ to the corresponding 2-hydroxyisoflavanone which then undergoes dehydration to yield the isoflavone.

In one aspect, the invention is a method for introducing into a naturally non-isoflavonoid-producing plant species the enzyme catalyzing the aryl migration of a flavanone to form an isoflavanone intermediate or an isoflavone, comprising introducing a DNA segment encoding the enzyme into the plant to form a transgenic plant, wherein the transgenic plant expresses the DNA segment under the control of a suitable constitutive or inducible promoter when the transgenic plant is exposed to conditions which permit expression. The DNA segment can comprise isolated genomic DNA or recombinant DNA. Preferably, the DNA segment is a CYP93C gene. An exemplary DNA segment from a soybean CYP93C gene consists essentially of the sequence from about nucleotide 36 to about nucleotide 1598 of the sequence depicted in SEQ ID NO:1. Another preferred DNA segment comprises a *Medicago truncatula* homolog of a CYP93C gene, more preferably, the sequence from about nucleotide 92 to about nucleotide 1657 of the sequence depicted in SEQ ID NO:4. Plants transformed by this method may also preferably express chalcone synthase, chalcone reductase, and chalcone isomerase genes to cause in vivo formation of daidzein or a daidzein derivative, and the chalcone synthase, chalcone reductase, and chalcone isomerase genes may also be transgenes. Plants transformed by this method may also preferably further comprise downstream genes, for example, isoflavone O-methyltransferase, isoflavone 2'-hydroxylase, isoflavone reductase, and vestitone reductase, to metabolize a formed isoflavone to biologically active isoflavonoid derivatives or conjugates. The plant can comprise isoflavone 4'-O-methyl-transferase to cause formation of biochanin A or a biochanin A derivative from the isoflavanone intermediate. An exemplary flavanone substrate for this transformation method is liquiritigenin and/or naringenin.

In another aspect, the present invention is a method for increasing the level of isoflavonoid compounds in naturally isoflavonoid-producing plants comprising introducing a DNA segment encoding the enzyme catalyzing the aryl migration of a flavanone to yield an isoflavonoid to form a transgenic plant, wherein the transgenic plant expresses the DNA segment under the control of a suitable constitutive or inducible promoter when the transgenic plant is exposed to conditions which permit expression. With this method, the resulting isoflavonoid can be an isoflavanone intermediate, an isoflavone, an isoflavone derivative, and an isoflavone conjugate. The DNA segment can comprise isolated genomic DNA or recombinant DNA. Preferably, the DNA segment is a CYP93C gene. An exemplary DNA segment from a soybean CYP93C gene consists essentially of the sequence from about nucleotide 36 to about nucleotide 1598 of the sequence depicted in SEQ ID NO:1. Another preferred DNA segment comprises a *Medicago truncatula* homolog of a CYP93C gene, more preferably, the sequence from about nucleotide 92 to about nucleotide 1657 of the sequence depicted in SEQ ID NO:4. An exemplary flavanone substrate for this transformation method is liquiritigenin and/or naringenin.

In another aspect, the invention is a method for synthesizing an isoflavanone intermediate or an isoflavone from a flavanone by expressing a recombinant CYP93C gene segment in a suitable bacterial, fungal, algal, or insect cell system. An exemplary gene segment consists essentially of the sequence from about nucleotide 36 to about nucleotide 1598 of the sequence depicted in SEQ ID NO:1. Another exemplary gene segment consists essentially of the sequence from about nucleotide 92 to about nucleotide 1657 of the sequence depicted in SEQ ID NO:4.

In another aspect, the invention is a method of reducing the levels of isoflavonoid compounds in a naturally isoflavonoid-producing plant comprising introducing and expressing an antisense or gene silencing construct that contains an intact CYP93C gene or segments thereof into the plant. An exemplary gene consists essentially of the sequence from about nucleotide 36 to about nucleotide 1598 of the sequence depicted in SEQ ID NO:1. Another exemplary gene consists essentially of the sequence from about nucleotide 92 to about nucleotide 1657 of the sequence depicted in SEQ ID NO:4.

In another aspect, the invention is a naturally non-isoflavonoid-producing plant cell transformed by introducing a DNA segment encoding the enzyme catalyzing the aryl migration of a flavanone to form an isoflavanone intermediate or an isoflavone, wherein the transformed plant cell expresses the DNA segment under the control of a suitable constitutive or inducible promoter when exposed to conditions which permit expression. The DNA segment can comprise isolated genomic DNA or recombinant DNA. Preferably, the DNA segment is a CYP93C gene. An exemplary DNA segment from a soybean CYP93C gene consists essentially of the sequence from about nucleotide 36 to about nucleotide 1598 of the sequence depicted in SEQ ID NO:1. Another preferred DNA segment comprises a *Medicago truncatula* homolog of a CYP93C gene, more preferably, the sequence from about nucleotide 92 to about nucleotide 1657 of the sequence depicted in SEQ ID NO:4. Plants transformed by this method may also preferably express chalcone synthase, chalcone reductase, and chalcone isomerase genes to cause in vivo formation of daidzein or a daidzein derivative, and the chalcone synthase, chalcone reductase, and chalcone isomerase genes may also be transgenes. Plants transformed by this method may also preferably further comprise downstream genes, for example, isoflavone O-methyltransferase, isoflavone 2'-hydroxylase, isoflavone reductase, and vestitone reductase, to metabolize a formed isoflavanone intermediate to biologically active isoflavonoid derivatives or conjugates. The plant can comprise isoflavone 4'-O-methyl-transferase to cause formation of biochanin A or a biochanin A derivative from the isoflavanone intermediate.

In another aspect, the invention is a naturally isoflavonoid-producing plant cell transformed by introducing a DNA segment encoding the enzyme catalyzing the aryl migration of a flavanone to yield an isoflavonoid to form a transformed plant cell, wherein the transformed plant cell expresses the DNA segment under the control of a suitable constitutive or inducible promoter when exposed to conditions which permit expression. With this method, the resulting isoflavonoid can be an isoflavanone intermediate, an isoflavone, an isoflavone derivative, and an isoflavone conjugate. The DNA segment can comprise isolated genomic DNA or recombinant DNA. Preferably, the DNA segment is a CYP93C gene. An exemplary DNA segment from a soybean CYP93C gene consists essentially of the sequence from about nucleotide 36 to about nucleotide 1598 of the sequence depicted in SEQ ID NO:1. Another preferred DNA segment comprises a *Medicago truncatula* homolog of a CYP93C gene, more preferably, the sequence from about nucleotide 92 to about nucleotide 1657 of the sequence depicted in SEQ ID NO:4.

In another aspect, the invention is a transgenic plant cell having reduced levels of isoflavonoid compounds, the plant cell transformed by introducing an antisense or gene silencing construct that contains an intact CYP93C gene or segments thereof into the plant cell. An exemplary gene consists essentially of the sequence from about nucleotide 36 to about nucleotide 1598 of the sequence depicted in SEQ ID NO:1. Another exemplary gene consists essentially of the sequence from about nucleotide 92 to about nucleotide 1657 of the sequence depicted in SEQ ID NO:4.

In another aspect, the invention is an isolated gene or DNA segment comprising a portion which encodes a cytochrome P450 that can catalyze the aryl migration of a flavanone to yield an isoflavanone intermediate or an isoflavone, wherein the portion consists essentially of about nucleotide 36 to about nucleotide 1598 of the sequence depicted in SEQ ID NO:1. An exemplary gene is the soybean gene encoding the enzyme catalyzing the aryl migration of liquiritigenin. Another exemplary gene is the soybean gene encoding the enzyme catalyzing the aryl migration of naringenin.

In another aspect, the invention is a protein encoded by a portion of an isolated gene or DNA segment which encodes a cytochrome P450 that can catalyze the aryl migration of a flavanone to yield an isoflavanone intermediate or an isoflavone, wherein the portion consists essentially of about nucleotide 36 to about nucleotide 1598 of the sequence depicted in SEQ ID NO:1.

In another aspect, the invention is an isolated gene or DNA segment comprising a portion which encodes a cytochrome P450 that can catalyze the aryl migration of a flavanone to yield an isoflavanone intermediate or an isoflavone, wherein the portion is a *Medicago truncatula* homolog of a CYP93C gene. An exemplary gene or DNA segment consists essentially of about nucleotide 92 to about nucleotide 1657 of the sequence depicted in SEQ ID NO:4. An exemplary gene is the *Medicago truncatula* gene encoding the enzyme catalyzing the aryl migration of liquiritigenin. Another exemplary gene is the *Medicago truncatula* gene encoding the enzyme catalyzing the aryl migration of naringenin.

In another aspect, the invention is a protein encoded by a portion of an isolated gene or a DNA segment which encodes a cytochrome P450 that can catalyze the aryl migration of a flavanone to yield an isoflavanone intermediate or an isoflavone, wherein the portion is a *Medicago truncatula* homolog of a CYP93C gene.

In yet another aspect, the invention is a food comprising edible transgenic plant material capable of being ingested for its nutritional value, wherein the transgenic plant has been transformed with an isolated gene or DNA segment which encodes a cytochrome P450 that can catalyze the aryl migration of a flavanone to yield an isoflavanone intermediate or an isoflavone, and wherein the transgenic plant exhibits increased levels of an isoflavonoid when compared to the level of the isoflavonoid in plants of the same species which do not comprise the isolated gene or DNA segment.

In yet another aspect, the invention is a food comprising at least one isoflavonoid, wherein the isoflavonoid is isolated from a transgenic plant transformed with an isolated gene or DNA segment which encodes a cytochrome P450 that can catalyze the aryl migration of a flavanone to yield an isoflavanone intermediate or an isoflavone, and wherein the transgenic plant exhibits increased levels of an isoflavonoid when compared to the level of the isoflavonoid in plants of the same species which do not comprise the isolated gene or DNA segment.

In yet another aspect, the invention is a composition comprising at least a portion of a transgenic plant transformed with an isolated gene or DNA segment which encodes a cytochrome P450 that can catalyze the aryl migration of a flavanone to yield an isoflavanone intermediate or an isoflavone, wherein the transgenic plant exhibits increased levels of an isoflavonoid when compared to the level of the isoflavonoid in plants of the same species which do not comprise the isolated gene or DNA segment, and wherein the composition is suitable for ingestion as a food stuff, a nutritional supplement, an animal feed supplement, or a nutraceutical.

In yet another aspect, the invention is a composition comprising an isoflavonoid suitable for administration as a food stuff, a nutritional supplement, an animal feed supplement, a nutraceutical, or a pharmaceutical, wherein the isoflavonoid is isolated from at least a portion of a transgenic plant transformed with an isolated gene or DNA segment which encodes a cytochrome P450 that can catalyze the aryl migration of a flavanone to yield an isoflavanone intermediate or an isoflavone, and wherein the transgenic plant exhibits increased levels of an isoflavonoid when compared to the level of the isoflavonoid in plants of the same species which do not comprise the isolated gene or DNA segment.

In yet another aspect, the invention is a method of increasing the nutritional value of a plant by transforming the plant with an isolated gene or DNA segment which encodes a cytochrome P450 that can catalyze the aryl migration of a flavanone to yield an isoflavanone intermediate or an isoflavone, wherein the transgenic plant exhibits increased levels of an isoflavonoid when compared to the level of the isoflavonoid in plants of the same species which do not comprise the isolated gene or DNA segment.

In yet another aspect, the invention is a method of using a transgenic plant transformed with an isolated gene or DNA segment which encodes a cytochrome P450 that can catalyze the aryl migration of a flavanone to yield an isoflavanone intermediate or an isoflavone, wherein the transgenic plant exhibits an increased level of an isoflavonoid when compared to the level of the isoflavonoid in plants of the same species which do not comprise the isolated gene or DNA segment, to provide a nutraceutical benefit to a human or animal administered the isoflavonoid. The isoflavonoid can be administered by ingestion of at least a portion of the plant. The isoflavonoid can also be administered by ingestion of a composition comprising an isoflavonoid isolated from the plant.

In yet another aspect, the invention is a method of using an isoflavonoid isolated from a transgenic plant transformed with an isolated gene or DNA segment which encodes a cytochrome P450 that can catalyze the aryl migration of a flavanone to yield an isoflavanone intermediate or an isoflavone, wherein the transgenic plant exhibits an increased level of an isoflavonoid when compared to the level of the isoflavonoid in plants of the same species which do not comprise the isolated gene or DNA segment, to provide a pharmaceutical benefit to a patient administered the isoflavonoid.

In yet another aspect, the invention is a method of increasing disease resistance in a plant by transforming the plant with an isolated gene or DNA segment which encodes a cytochrome P450 that can catalyze the aryl migration of a flavanone to yield an isoflavanone intermediate or an isoflavone, wherein the transgenic plant exhibits an increased level of an isoflavonoid when compared to the level of the isoflavonoid in plants of the same species which do not comprise the isolated gene or DNA segment.

In yet another aspect, the invention is a method of increasing nodulation efficiency of a leguminous plant by transforming the plant with an isolated gene or DNA segment which encodes a cytochrome P450 that can catalyze the aryl migration of a flavanone to yield an isoflavanone intermediate or an isoflavone, wherein the transgenic plant exhibits an increased level of an isoflavonoid released from the roots when compared to the level of the isoflavonoid released from the roots of plants of the same species which do not comprise the isolated gene or DNA segment.

In yet another aspect, the invention is a transgenic leguminous plant exhibiting increased nodulation efficiency transformed with an isolated gene or DNA segment which encodes a cytochrome P450 that can catalyze the aryl migration of a flavanone to yield an isoflavanone intermediate or an isoflavone, wherein the transgenic plant exhibits an increased level of an isoflavonoid released from the roots when compared to the level of the isoflavonoid released from the roots of plants of the same species which do not comprise the isolated gene or DNA segment.

In yet another aspect, the invention is a method of increasing bacterial or fungal symbiosis in a plant by transforming the plant with an isolated gene or DNA segment which encodes a cytochrome P450 that can catalyze the aryl migration of a flavanone to yield an isoflavanone intermediate or an isoflavone, wherein the transgenic plant exhibits an increased level of an isoflavonoid when compared to the level of the isoflavonoid in plants of the same species which do not comprise the isolated gene or DNA segment.

In yet another aspect, the invention is a transgenic plant exhibiting increased bacterial or fungal symbiosis transformed with an isolated gene or DNA segment which encodes a cytochrome P450 that can catalyze the aryl migration of a flavanone to yield an isoflavanone intermediate or an isoflavone, wherein the transgenic plant exhibits an increased level of an isoflavonoid when compared to the level of the isoflavonoid in plants of the same species which do not comprise the isolated gene or DNA segment.

In yet another aspect, the invention is a transgenic plant comprising at least one recombinant DNA sequence encoding a cytochrome P450 that can catalyze the aryl migration of a flavanone to yield an isoflavanone intermediate or an isoflavone, wherein the transgenic plant exhibits an increased level of an isoflavonoid when compared to the level of the isoflavonoid in plants of the same species which do not comprise the recombinant DNA sequence.

In yet another aspect, the invention is seed from a transgenic plant comprising at least one recombinant DNA sequence encoding a cytochrome P450 that can catalyze the aryl migration of a flavanone to yield an isoflavanone intermediate or an isoflavone, wherein the transgenic plant exhibits an increased level of an isoflavonoid when compared to the level of the isoflavonoid in plants of the same species which do not comprise the recombinant DNA sequence.

In yet another aspect, the invention is progeny from a transgenic plant comprising at least one recombinant DNA sequence encoding a cytochrome P450 that can catalyze the aryl migration of a flavanone to yield an isoflavanone intermediate or an isoflavone, wherein the transgenic plant exhibits an increased level of an isoflavonoid when compared to the level of the isoflavonoid in plants of the same species which do not comprise the recombinant DNA sequence.

In yet another aspect, the invention is progeny from seed of a transgenic plant comprising at least one recombinant DNA sequence encoding a cytochrome P450 that can catalyze the aryl migration of a flavanone to yield an isoflavanone intermediate or an isoflavone, wherein the transgenic plant exhibits an increased level of an isoflavonoid when compared to the level of the isoflavonoid in plants of the same species which do not comprise the recombinant DNA sequence.

In yet another aspect, the invention is use of a transgenic plant transformed with an isolated gene or DNA segment which encodes a cytochrome P450 that can catalyze the aryl migration of a flavanone to yield an isoflavanone intermediate or an isoflavone, wherein the transgenic plant exhibits an increased level of an isoflavonoid when compared to the level of the isoflavonoid in plants of the same species which do not comprise the isolated gene or DNA segment, for the preparation of a nutraceutical preparation for achieving a nutritional effect.

In yet another aspect, the invention is use of a transgenic plant transformed with an isolated gene or DNA segment which encodes a cytochrome P450 that can catalyze the aryl migration of a flavanone to yield an isoflavanone intermediate or an isoflavone, wherein the transgenic plant exhibits an increased level of an isoflavonoid when compared to the level of the isoflavonoid in plants of the same species which do not comprise the isolated gene or DNA segment, for the preparation of a pharmaceutical preparation for achieving a therapeutic effect.

DETAILED DESCRIPTION

One aspect of the present invention is an isolated gene which encodes the first step of the isoflavone synthase reaction: a cytochrome P450 that can catalyze the aryl migration of a flavanone to yield an isoflavone. Genes and corresponding cDNA of the soybean or *Medicago truncatula* CYP93 family have been isolated. The enzymes encoded by the genes of the present invention are isoflavone synthases (IFS) and can catalyze the aryl migration of a flavanone to yield an isoflavone either directly or through the intermediacy of a 2-hydroxyisoflavanone. One isolated soybean gene is classified as CYP93C1v2.

Cytochrome P450 enzymes belong to a large superfamily of enzymes that are abundant in every living organism. The P450 nomenclature committee has determined that each P450 should carry a "CYP" designation and arbitrarily divided the superfamily into families (alphabetical designation), subfamilies (numerical designation) and allelic variants ("v" plus numerical designation) based on amino acid identity of >40%, >55%, and >97%, respectively (Nelson, et al. 1993. "The P450 superfamily update on new sequences, gene mapping, accession numbers, early trivial names of enzymes, and nomenclature," *DNA Cell Biol* 12:1). Thus, CYP93C1v2 is a variant of the first described P450 belonging to the third subfamily (C) of the ninety-third P450 family.

Utilizing the procedures presented herein, any plant known to produce isoflavonoids may also serve as sources of suitable DNA, or coding sequences may be synthesized in vitro based on the sequences for the IFS genes of the present invention. CYP93 family members can also be obtained from other plant species by polymerase chain reaction amplification methods known to those skilled in the art, using primer sequences corresponding to regions of nucleotide conservation between CYP93 family members. Furthermore, the genes of the present invention are defined by their catalytic activity: the aryl migration of a flavanone to yield an isoflavone. The gene sequences presented as SEQ ID NO:1 and SEQ ID NO:4 are exemplary, and it is understood that modifications to these genes which do not alter the catalytic activity of its encoded protein fall within the scope of the present invention. While a preferred IFS gene contains the entire open reading frame, portions of or the entire 5' and 3' untranslated regions as well as portions of the vector sequence can also be present. With the isolation and functional identification of these isoflavone synthase (IFS) genes that encode the first key step in isoflavone formation, the aryl migration reaction, it is now possible to introduce the isoflavonoid pathway into all plant species, including those that do not naturally possess this pathway.

Another aspect of the present invention is a genetically modified plant which has been transformed with a gene of the present invention. For example, when the CYP93C1v2 gene is transferred into the model plant *Arabidopsis thaliana*, which does not naturally produce isoflavonoids, the isoflavone genistein accumulates as a series of glyco-conjugates (Example 1). This demonstrates that the genes of the present invention can be genetically engineered into plants which do not naturally contain the isoflavonoid pathway, and the transgenic plants can then produce isoflavonoids, resulting in plants with improved disease resistance and/or value added health benefits for humans. In the present invention, unless otherwise stated, as used herein, the term "plant" or "progeny" includes plant parts, plant tissue, plant cells, plant protoplasts, plant cell tissue cultures from which plants can be regenerated, plant calli, plant clumps, explants, plant cells that are intact in plants, or parts of plants, such as embryos, pollen, ovules, flowers, capsules, stems, leaves, seeds, roots, root tips, and the like. Furthermore, the present invention includes the IFS genes expressed in various parts of the plant, e.g., in aerial portions of the plant useful for increasing disease resistance or production of health promoting isoflavonoid nutraceuticals, in seeds useful for increasing levels of isoflavones and their conjugates, or in roots useful for increasing disease resistance or production of nodulation gene inducing isoflavones.

In another aspect, the present invention is a method of improving disease resistance and a transgenic plant with increased disease resistance. By transforming a plant which does not naturally make isoflavones with an IFS gene of the present invention, disease resistance can be genetically engineered into the plant by providing the necessary enzyme to convert its natural flavanones into isoflavonoids. The introduction and subsequent expression of an IFS gene of the present invention into a crop species which naturally possesses the isoflavonoid pathway results in increased levels of the isoflavonoid defense compounds.

In another aspect, the present invention is a method of increasing levels of isoflavonoids that might be beneficial to the establishment of bacterial or fungal symbioses with plants and a transgenic plant with an increased capacity for symbiotic association with bacteria or fungi. Bacterial nodulation can be stimulated in transgenic leguminous plants by expression of an IFS gene of the present invention and decreased by expression of antisense constructs or constructs designed to promote gene silencing that contain an intact IFS gene or segments thereof. Mycorrhizal colonization of leguminous plants can also be increased through the introduction and expression of an IFS gene of the present invention.

In yet another aspect, the present invention is a method of producing isoflavonoid compounds in plants or any other organism to be used in nutraceuticals or pharmaceuticals to confer human or animal health benefits. Edible transgenic plants high in isoflavonoids can be utilized as food for humans and animals. Edible compositions high in isoflavonoids can also be made by incorporation of the transgenic plants or plant materials, or by incorporation of isoflavonoids isolated from the transgenic plants. Compositions useful for administration as a food stuff, a nutritional supplement, an animal feed supplement, a nutraceutical, or a pharmaceutical can be made by incorporation of the transgenic plants or plant materials, or by incorporation of isoflavonoids isolated from the transgenic plants. The nutritional value of a plant can be increased by transforming the plant with an IFS gene of the present invention and, as a result, accumulating high amounts of isoflavonoids in the plant.

The soybean IFS gene of the present invention was isolated and purified according to the detailed procedures outlined in Example 2. The DNA sequence is shown in SEQ ID NO:1 and FIG. 2, and the encoded protein sequence of the isolated soybean CYP93C clone is shown in SEQ ID NO:2 and FIG. 3. For comparison, FIG. 3 also shows the protein sequence alignment between the isolated CYP93C clone (SEQ ID NO:2) and CYP93B1 (SEQ ID NO:3), the licorice licodione synthase.

The DNA and protein sequences of the soybean CYP93C1 open reading frame were deposited in the Genbank data base under accession # AF022462. The deposition was made by Siminszky, Dewey and Corbin, and the sequence described as representing a gene induced in soybean in response to herbicide safeners. However, the function of the gene was not known and there was no understanding that it could be involved in isoflavonoid biosynthesis at the time the deposit was made (Siminszky, B., Corbin, F. T., Ward, E. R., Fleischmann, T. J. and Dewey, R. E., 1999, "Expression of a soybean cytochrome P450 monooxygenase cDNA in yeast and tobacco enhances the metabolism of phenylurea herbicides." *Proc. Natl. Acad. Sci. USA* 96: 1750–1755). The sequence of the clone characterized herein differs from CYP93C1 in three nucleotide substitutions in the open reading frame that change proline 140 to leucine, threonine 156 to isoleucine, and glutamate 295 to lysine. Thus, the soybean gene identified herein has been classified as CYP93C1v2.

The cDNA insert from CYP93C1v2 was used to probe 240,000 phage plaques from a *Medicago truncatula* root cDNA library (van Buuren, M. L., I. E. Maldonado-Mendoza, A. T. Trieu, L. A. Blaylock, and M. J. Harrison, 1999, "Novel genes induced during an arbuscular mycorrhizal (AM) symbiosis formed between *Medicago truncatula* and *Glomus versiforme*," *Mol. Plant-Microbe Interact.* 12, 171–181). Five positive plaques were purified, in vivo excised, and sequenced. A full length clone designated mtIFSE3 was completely sequenced on both strands, and shown to encode the *Medicago truncatula* homolog of soybean CYP93C1. The nucleotide sequence of mtIFSE3 is shown in SEQ ID NO:4 and FIG. 4, and the protein sequence, in SEQ ID NO:5. An alignment between the protein sequences of mtIFSE3 and CYP93C1v2 is shown in FIG. 5.

An IFS gene of the soybean or *Medicago truncatula* CYP93C subfamily or corresponding cDNA sequence, the open reading frame of which encodes a cytochrome P450 that can catalyze the aryl migration of a flavanone to yield an isoflavone, either directly or through the intermediacy of a 2-hydroxyisoflavanone, can be used to introduce the isoflavonoid pathway into any plant species that does not naturally possess this pathway. Soybean CYP93C1v2 acts on the flavanones liquiritigenin to yield daidzein, and naringenin to yield genistein. Liquiritigenin is only formed in plants that possess the enzyme chalcone reductase (CHR) (Welle, R. and Grisebach, H., 1989, "Phytoalexin synthesis in soybean cells: elicitor induction of reductase involved in biosynthesis of 6'-deoxychalcone." *Arch Biochem Biophys* 272: 97–102), and a form of chalcone isomerase that is active against 2',4,4'-trihydroxychalcone, the product of the co-action of chalcone synthase (CHS) with CHR (Dixon, R. A., Blyden, E. R., Robbins, M. P., van Tunen, A. J. and Mol, J. N. M., 1988, "Comparative biochemistry of chalcone isomerases." *Phytochemistry* 27: 2801–2808). Such genes are common in legumes, but not in most other plant families. Thus, to form daidzein in transgenic plants that do not possess the isoflavonoid pathway, it would be necessary to introduce three new genes, namely CHR, to co-act with CHS to form 2',4,4'-trihydroxychalcone, a suitable CHI to convert 2',4,4'-trihydroxychalcone to liquiritigenin, and IFS, assuming that the 2-hydroxyisoflavanone intermediate can spontaneously dehydrate in planta, a phenomenon that is demonstrated below. Without CHR present, no liquiritigenin would be formed, and IFS would only be able to act on naringenin to yield, assuming spontaneous dehydration of the 2-hydroxyisoflavanone, genistein.

The IFS genes of the present invention can be introduced into non-leguminous plants such as by standard *Agrobacterium*-based or biolistic transformation procedures (Horsch, et al., 1985, "A simple and general method for transferring genes into plants," *Science* 227:1229–1231; and Klein, et al., 1988, "Stable genetic transformation of intact *Nicotiana* cells by the particle bombardment process," *Proc Natl Acad Sci USA* 85:8502–8505). Both procedures require the construction of a plasmid vector containing a desirable transcriptional promoter driving expression of the gene of interest (in this case IFS), followed by a transcriptional terminator and a selectable marker gene for resistance, such as to an antibiotic or a herbicide. The biolistic procedure coats metal particles with plasmid DNA containing the gene of interest and places them on a micro carrier disk. Using the biolistic apparatus, the particles are physically propelled into plant tissue. The plant tissue is then put under selection (e.g., antibiotic or herbicide) followed by regeneration. The two *Agrobacterium*-based procedures are "in planta" and "ex-planta", respectively. Both procedures require the above gene construct to be placed into a T-DNA vector, which is then transferred into *Agrobactrium* tumefaciens. The in planta procedure places the transformed *Agrobacterium* in the presence of plant material (flower or meristem) and the plants are allowed to seed followed by selection (e.g., antibiotic or herbicide) during germination. The ex-planta procedure also places *Agrobacterium* in the presence of plant material (callus, cell culture, leaf disk, hypocotyl) which is placed directly under selection (e.g., antibiotic or herbicide) followed by regeneration.

Thus, the isoflavonoid pathway can be introduced into any plant species that does not possess the enzyme catalyzing the IFS reaction by expressing the IFS gene in transgenic plants under the control of a suitable constitutive or inducible promoter.

EXAMPLE 1

Transformation of *Arabidopsis thailiana* with Soybean CYP93C1V2

Soybean CYP93C1v2 cDNA was placed in the binary plant transformation vector pCHF3, in which it is under control of the cauliflower mosaic virus 35S promoter, using standard recombinant DNA methods (Sambrook, et al. 1989. *Molecular Cloning. A Laboratory Manual,* 2nd Ed, Cold Spring Harbor Laboratory Press, New York). The gene was then transformed into plants of the crucifer, *Arabidopsis thaliana* ecotype Columbia, using *Agrobacterium tumefaciens* and a standard floral infiltration procedure (Clough, S. J. and Bent, A. F., 1998, "Floral dip: a simplified method for *Agrobacterium*-mediated transformation of *Arabidopsis thaliana*". *Plant J* 16: 735–743). Transgenic plants were selected by germinating the seedlings on kanamycin, and those surviving selection were allowed to set seed. $T_2$ seedlings expressing CYP93C1v2 were identified by standard DNA and RNA gel blot analysis (Sambrook, et al. 1989. *Molecular cloning. A Laboratory Manual,* 2nd Ed, Cold Spring Harbor Laboratory Press, New York), and analyzed for accumulation of genistein in leaves by HPLC analysis, according to a method developed to profile the flavonoid components of *Arabidopsis* leaves (Graham, T. L., 1998, "Flavonoid and flavonol glycoside metabolism in *Arabidopsis*". *Plant Physiol Biochem* 36: 135–144).

Figure 6A:
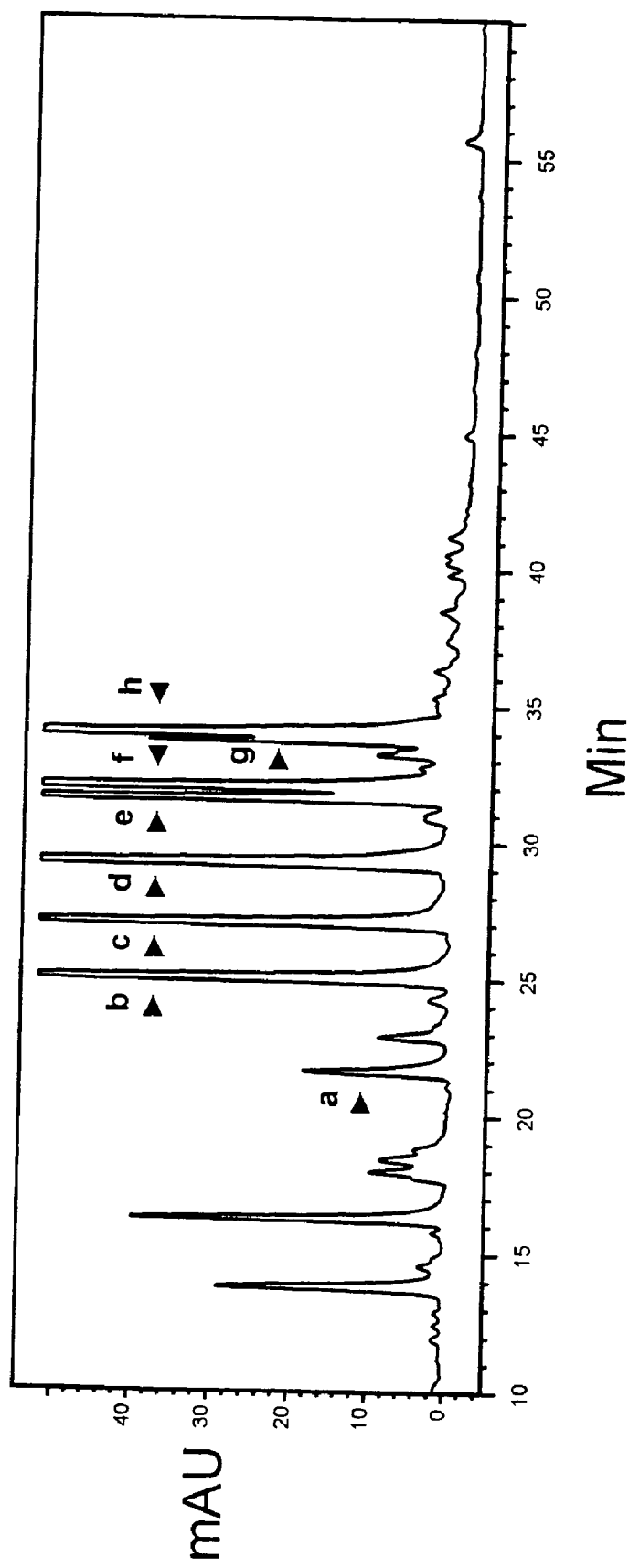
FIG. 6A and FIG. 6B depict HPLC traces of extracts from pooled tissues (leaves, shoots, flowers) of *Arabidopsis thaliana* ecotype Columbia harboring an empty tDNA vector (FIG. 6A) and *Arabidopsis thaliana* ecotype Columbia harboring the soybean CYP93C1v2 cDNA sequence (FIG. 6B). The empty vector transformed line contains a number of flavonol glycosides and other phenolic compounds that are also present in the CYP93C1v2 transformed line. These compounds were identified as (a) rhamnose (Rha)-glucose (Glc)-quercetin (Q), (b) uncharacterized conjugate of Q, (c) Rha-Glc-Rha-Kaempferol (K), (d) Glu-Rha-Q, (e) Rha—Rha-Q, (f) Glc-Rha-K, (g) sinapic acid, (h) Rha—Rha-K. Three additional compounds were observed in the CYP93C1v2 transformed line (FIG. 6B), and labeled "1," "2" and "3.
Figure 6B:
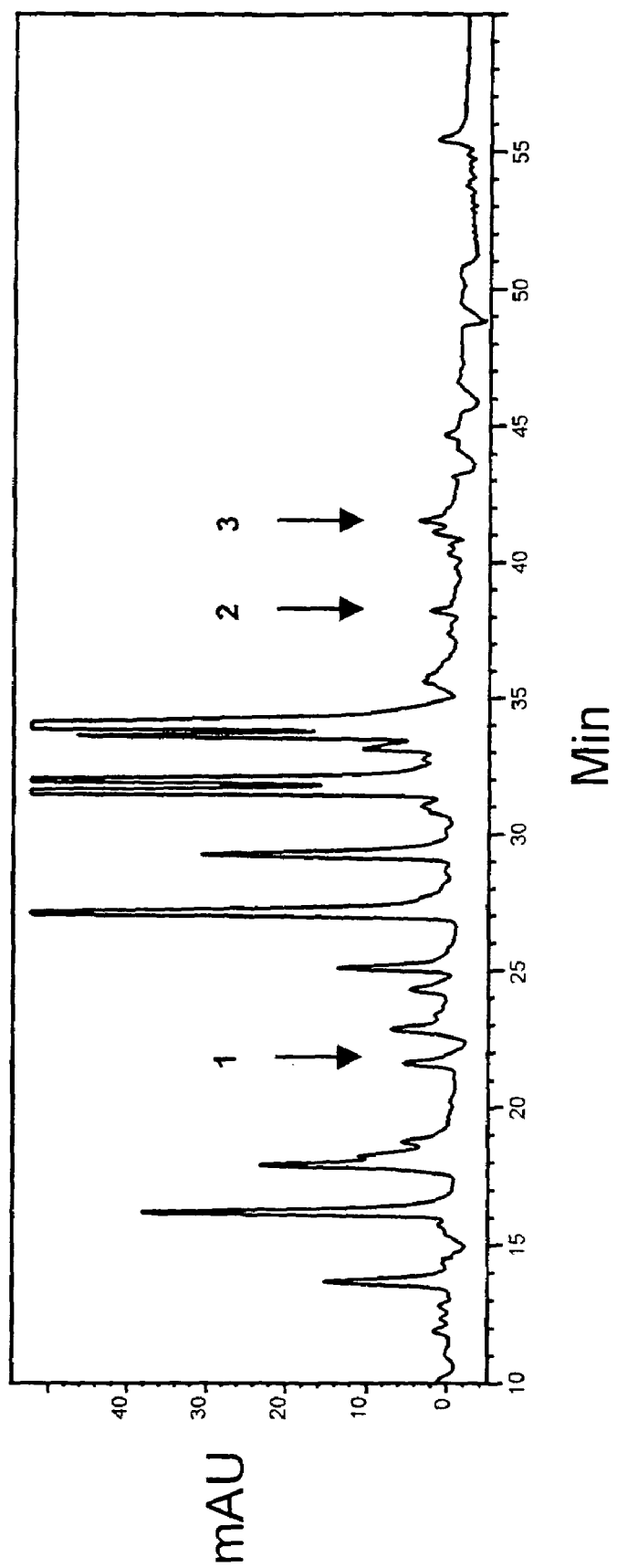
Figure 6C:
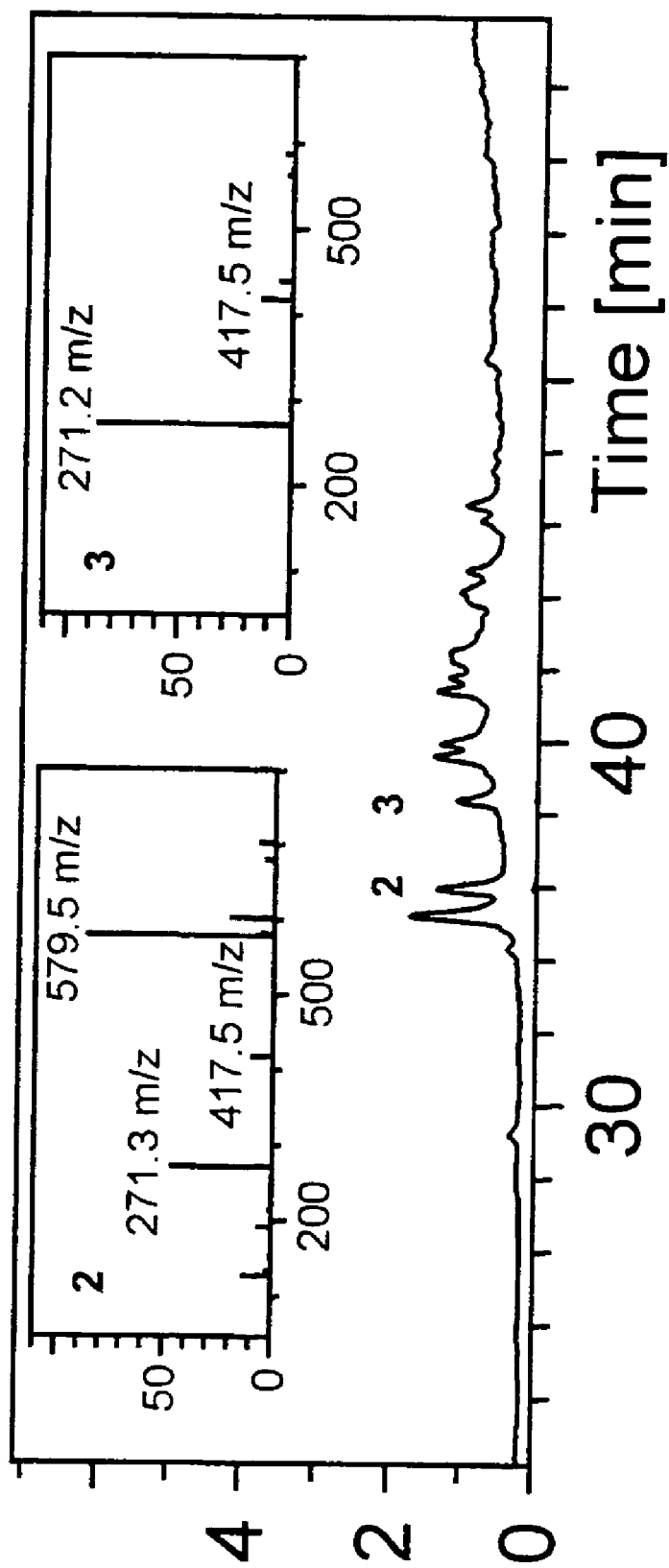
" FIG. 6C depicts a total ion chromatogram of partially purified peaks 2 and 3, and the insets show the specific ions generated from these compounds. Peak 2 has a parental molecular mass ion of 579.5 consistent with genistein conjugated to a glucose-rhamnose disaccharide, and two further mass ions of 417.5 and 271.3, representing Rha-genistein and free genistein, respectively. Peak 3, which has a parental molecular ion of mass 417.5, is thereby identified as Rha-genistein.
Figure 7A:
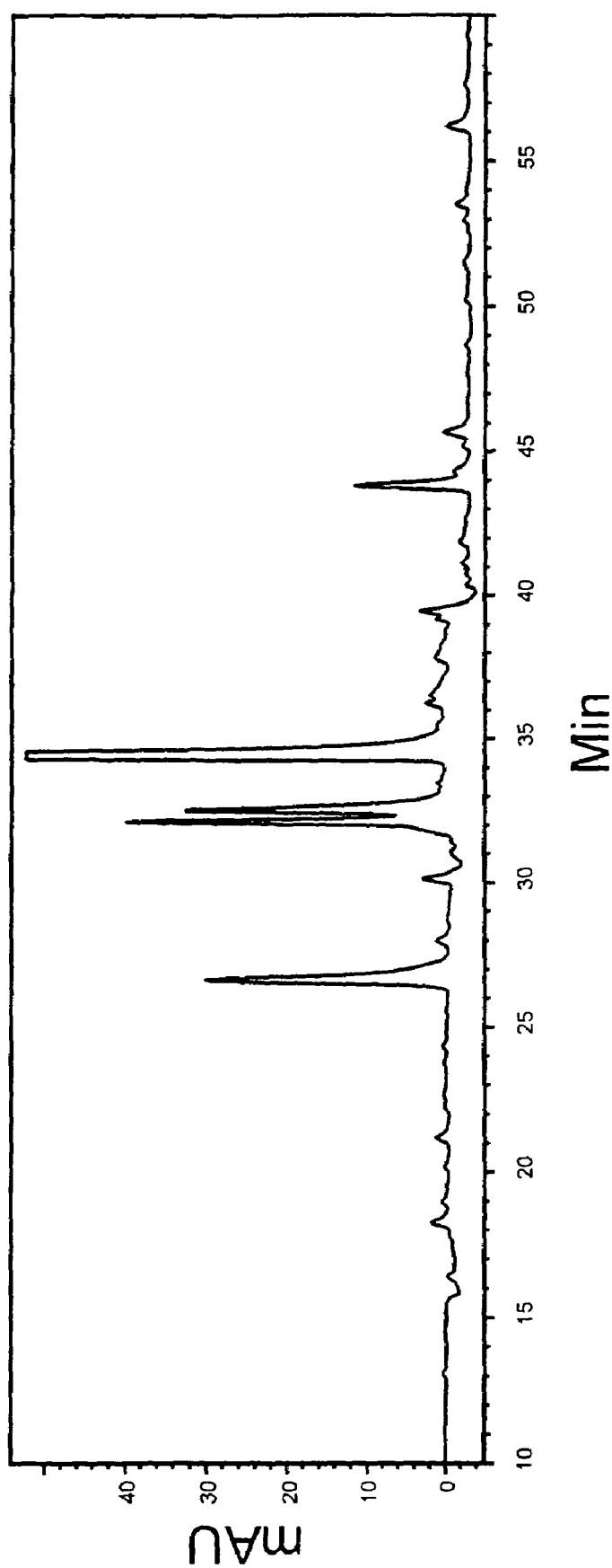
FIG. 7A and FIG. 7B depict HPLC traces of the same extracts as shown in FIG. 6A (empty-vector transformed) and FIG. 6B, (CYP93C1v2 transformed), but following digestion with α-glucosidase. Peaks 2 and 3 remained at the same retention time as in FIGS. 6A and 6B. However, Peak 1 disappeared, and was replaced with a new Peak 4 of much later retention time.
Figure 7B:
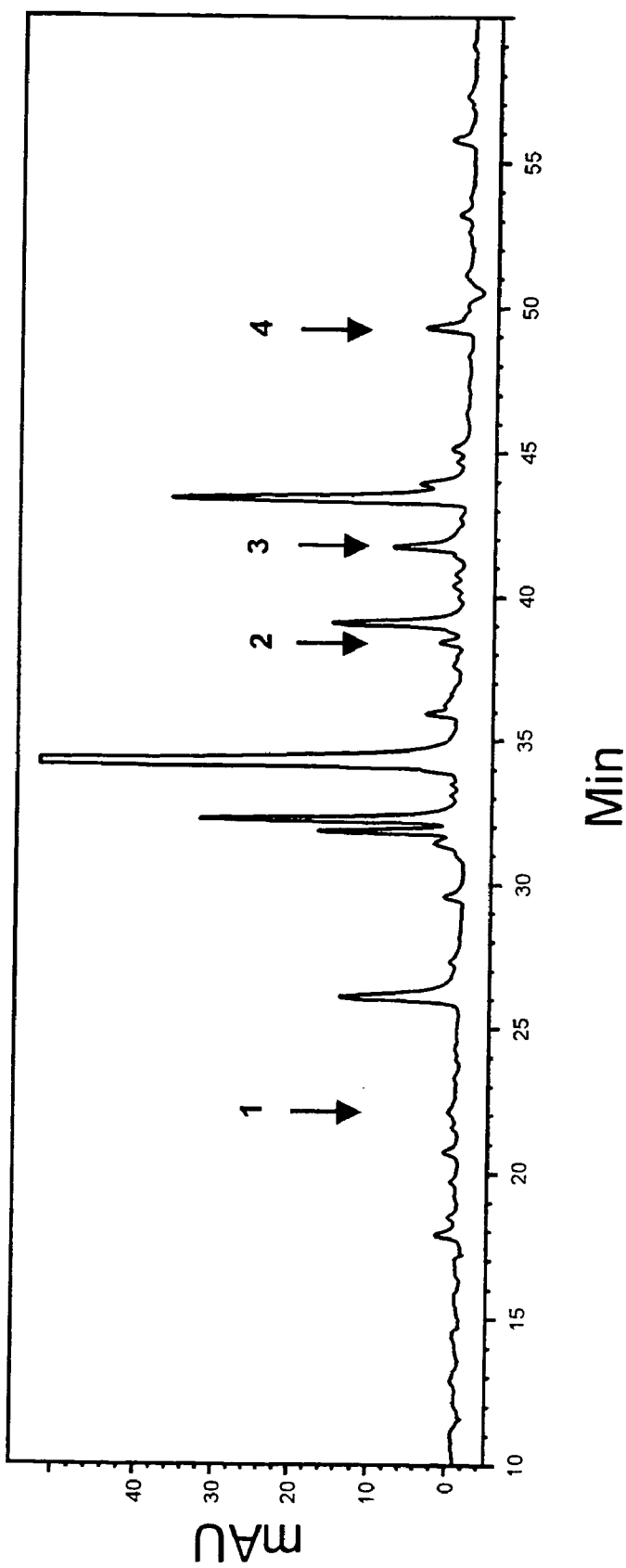
Figure 7C:
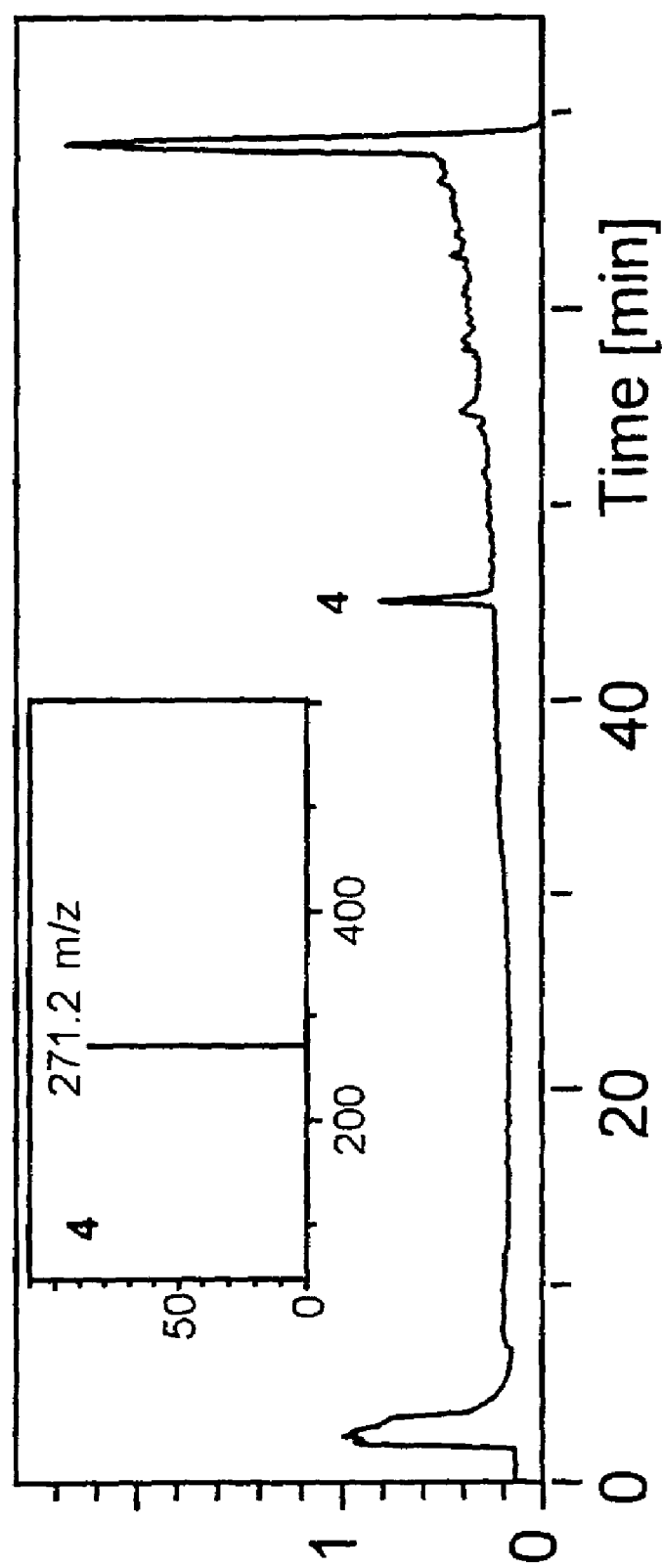
FIG. 7C shows the total ion chromatograph of purified Peak 4, and the inset shows the parental molecular ion, with mass of 271.2, consistent with Peak 4 being free genistein.
Figure 7D:
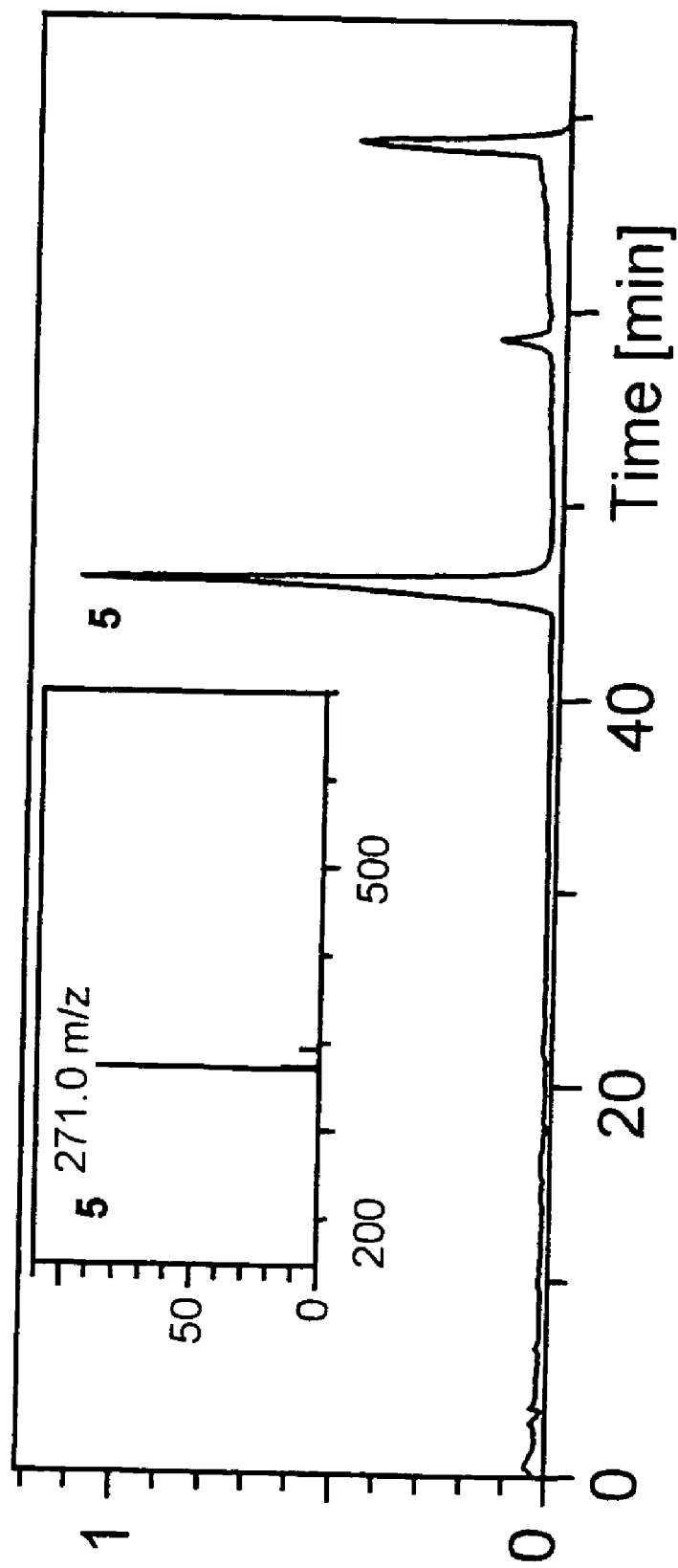
FIG. 7D shows a total ion chromatograph, and the parental molecular ion, of an authentic sample of genistein.

FIG. 6A shows a typical HPLC trace of a leaf extract from an untransformed plant. The major components are glycosides (containing glucose and rhamnose) of the flavonols kaempferol and quercetin. Plants harboring the soybean CYP93C1v2 gene showed an additional three peaks on HPLC analysis (FIG. 6B), indicated by the arrows labeled as "1," "2" and "3." No free genistein, free 2-hydroxyisoflavanone or 2-hydroxyisoflavanone conjugates were observed. However, following treatment of extracts with almond β-glucosidase (FIG. 7B), one of the new peaks disappeared, and free genistein was now observed, consistent with the peak being a glucoside of genistein. LC-MS analysis confirmed the identities of the new compounds as a glucoside of genistein, glucose-rhamnose-genistein, and rhamnose-genistein (FIGS. 6C and 7C and 7D, insets). Therefore, expression of CYP93C1v2 in transgenic *Arabidopsis* leads to formation of genistein with no requirement for an enzyme to catalyze the dehydration of the presumed 2-hydroxyisoflavanone intermediate. *Arabidopsis* plants then modify the genistein by exactly the same chemistry they use to conjugate their endogenous flavonols, namely by conjugation to glucose and rhamnose. Transgenic production of conjugates of genistein are suitable for nutraceutical applications, because genistein is also glycosylated in soybean, its natural dietary source (Graham, T. L., 1991, "Flavonoid and isoflavonoid distribution in developing soybean seedling tissues and in seed and root exudates." *Plant Physiol* 95: 594–603).

In addition to introducing the isoflavonoid pathway into plants that do not possess this pathway, the level of isoflavonoid compounds can be controlled in plants that do possess the pathway by manipulating the level of expression of the IFS gene. Increasing the levels of isoflavonoid compounds in leguminous plants by expression of the IFS gene of the present invention in transgenic plants under the control of a suitable constitutive or inducible promoter can be accomplished by standard methods such as *Agrobacterium*-based or biolistic transformation methods known in the art. Alternatively, the level of isoflavonoid compounds in plants can be reduced by expression of antisense constructs or constructs designed to promote gene silencing that contain an intact IFS gene, or segments thereof, in transgenic plants using methods known in the art. (Bourque, J. E., 1995, "Antisense strategies for genetic manipulations in plants," *Plant Science* 105:125–149; and Angell, S. M. and D. C. Baulcombe, 1997, "Consistent gene silencing in transgenic plants expressing a replicating potato virus X RNA," *EMBO J.* 16:3675–3684). Antisense constructs for gene silencing are constructed by placing the whole or part of the cDNA in a three prime to five prime orientation behind a desirable transcriptional promoter and ahead of a transcriptional terminator in a plasmid vector. The vector may be used for biolistic transformation or the new antisense gene may be transferred to a T-DNA vector for *Agrobacterium*-based transformation. The actual mechanism of silencing by antisense constructs is unknown. Homology-dependent gene silencing or co-suppression requires the over-expression of a homologous gene; therefore, to achieve co-suppression a construct is made using a strong promoter, the gene of interest (in this case IFS) and a transcriptional terminator. The gene should be transferred to plants as described above. Gene silencing is an epigenetic phenomenon that may or may not occur with a particular gene construct. When it does occur, the inhibition of gene expression can be greater than with the antisense approach.

Isoflavones can be synthesized from flavanones, utilizing recombinant IFS expressed in any suitable bacterial, fungal, algal, or insect cell system. For example, naringenin is extracted in large amounts from grapefruits. A CYP93C1 enzyme can be used convert naringenin to 2,5,7,4'-tetrahydroxyisoflavanone, which spontaneously converts to the valuable nutraceutical genistein under weak acid conditions. Furthermore, daidzin can be synthesized from liquiritigenin utilizing recombinant CYP93C1 and an isoflavone glucosyltransferase (Köster, J. and W. Barz, 1981, "UDP-Glucose: isoflavone 7-O-glucosyltransferase from roots of chick pea (*Cicer arietinum* L.)." *Arch Biochem Biophys* 212: 98–104).

EXAMPLE 2

Methodology Used to Isolate and Identify IFS cDNA Clones

In an attempt to obtain cDNA clones encoding IFS, a functional genomics approach was followed. IFS activity is present in soybean seeds, which accumulate daidzein and genistein. Furthermore, IFS activity can be induced in soybean tissues in response to infection with *Phylophthora infestans*, associated with the accumulation of the isoflavonoid phytoalexin glyceollin (Bhattacharyya, M. K. and E. W. B. Ward, 1987, "Biosynthesis and metabolism of glyceollin I in soybean hypocotyls following wounding or inoculation with *Phytophthora megasperma* f. sp. *glycinea,*" *Physiol Mol Plant Path* 31: 387–405). It was also known that an enzyme catalyzing a similar reaction to IFS, namely the 2-hydroxylation of flavanone but without aryl migration, belongs to the CYP93B1 subclass of cytochrome P450s (Akashi, et al, 1998, "Identification of a cytochrome P450 cDNA encoding (2S)-flavanone 2-hydroxylase of licorice (*Glycyrrhiza echinata* L.: *Fabaceae*) which represents licodione synthase and flavone synthase II," *FEBS Letters* 431: 287–290). We therefore searched an expressed sequence tag (EST) database of partial soybean sequences obtained by mass sequencing of two cDNA libraries: a *Phytophthora*-infected hypocotyl cDNA library (48 hours after infection) and a mid to late developmental stage seed library. Nine candidate P450 sequences were identified, of which three belonged to the CYP93 family. DNA probes were made from the EST clones of the three CYP93 candidates and were used to probe an RNA blot of transcripts from alfalfa suspension cells at various times after exposure to yeast elicitor, a treatment known to induce IFS activity at the onset of isoflavonoid phytoalexin accumulation (Kessmann, et al., 1990, "Stress responses in alfalfa (*Medicago sativa* L.) III. Induction of medicarpin and cytochrome P450 enzyme activities in elicitor-treated cell suspension cultures and protoplasts," *Plant Cell Reports* 9: 38–41). One P450 probe cross-hybridized and detected alfalfa transcripts that were strongly induced by elicitation. This probe was derived from a clone with high homology to soybean CYP93C1 as described below, and the insert in the EST clone was full length. The insert was excised and then cloned into the baculovirus expression system for functional identification by heterologous expression in insect cells (Pauli, H. H. and T. M. Kutchan, 1998, "Molecular cloning and functional heterologous expression of two alleles encoding (S)-N-methylcoclaurine 3' hydroxylase (CYP80B1), a new methyl jasmonate-inducible cytochrome P450-dependent monooxygenase of benzylisoquinoline alkaloid biosynthesis," *The Plant J* 13: 793–801).

Figure 8A:
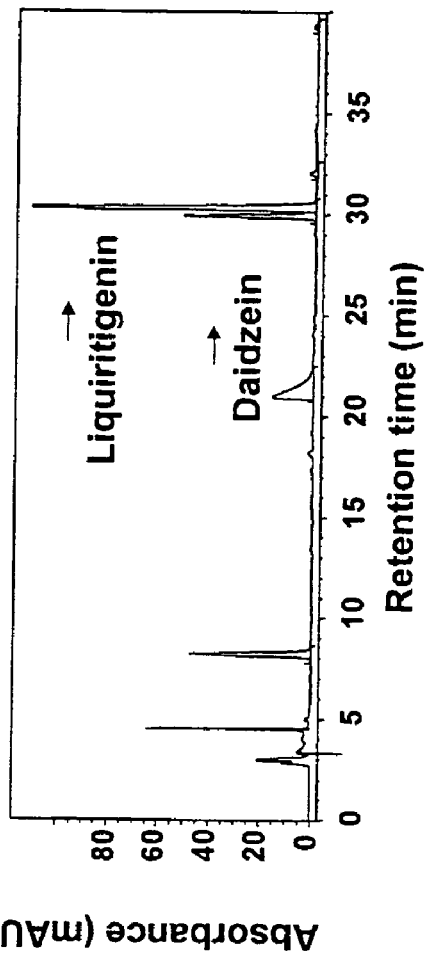
FIGS. 8A, 8B, 8C and 8D are high performance liquid chromatography (HPLC) chromatograms depicting the presence of new peaks at RT 29.96 and 37.7 min representing the presence of the isoflavone daidzein formed from the flavanone liquiritigenin, or the isoflavone genistein formed from the flavanone naringenin, in insect cell microsomes expressing CYP93C1v2.
Figure 8B:
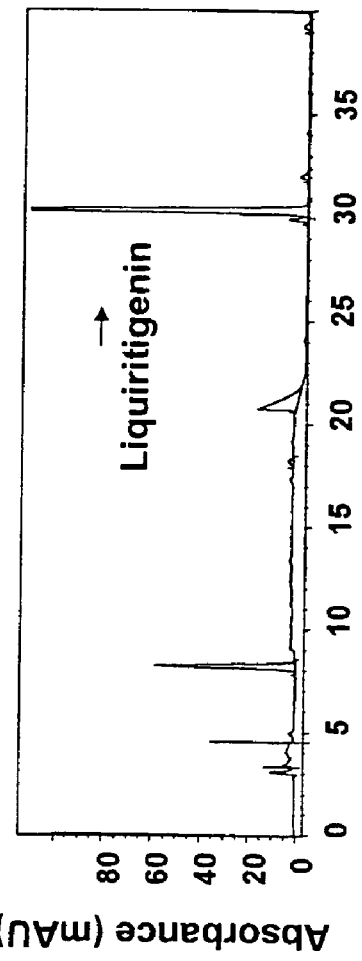
Figure 8C:
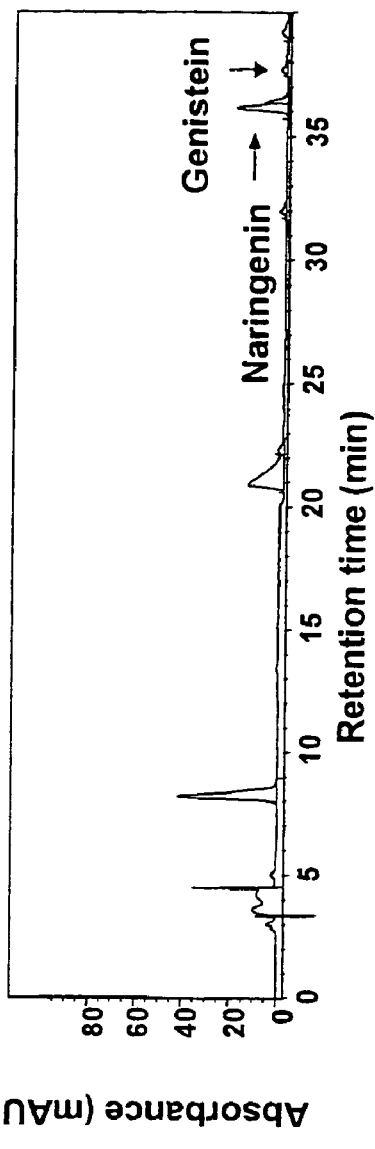
Figure 8D:
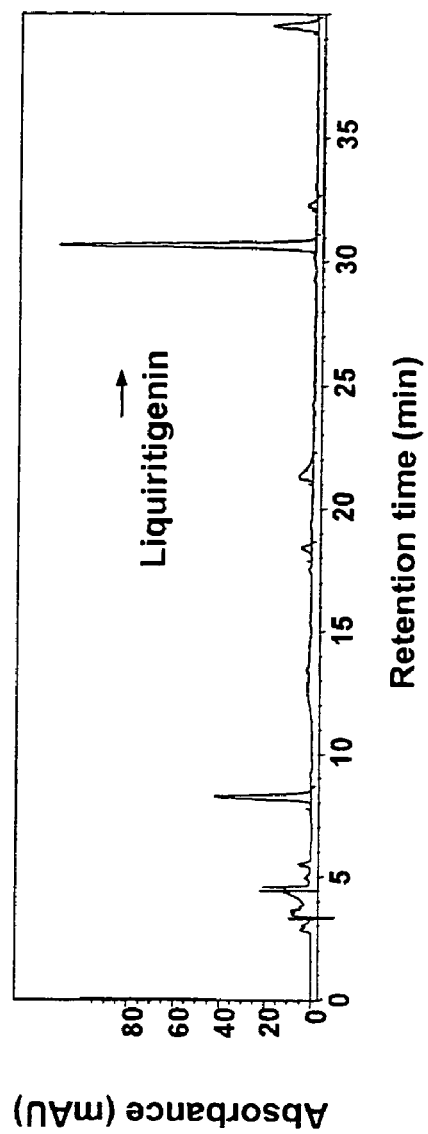
Figure 9A:
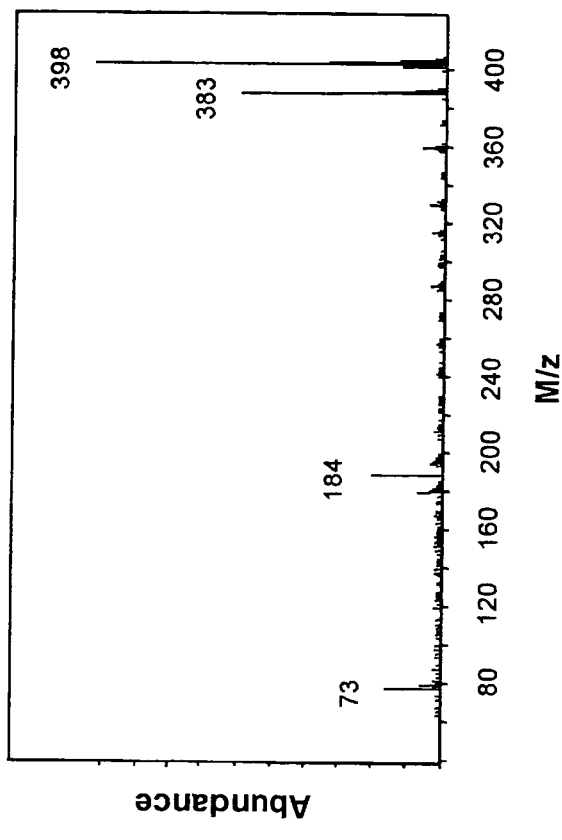
FIG. 9A and FIG. 9B are mass spectra of BSTFA (N,O-bis(trimethylsilyl) trifluoroacetamide) derivatives.
Figure 9B:
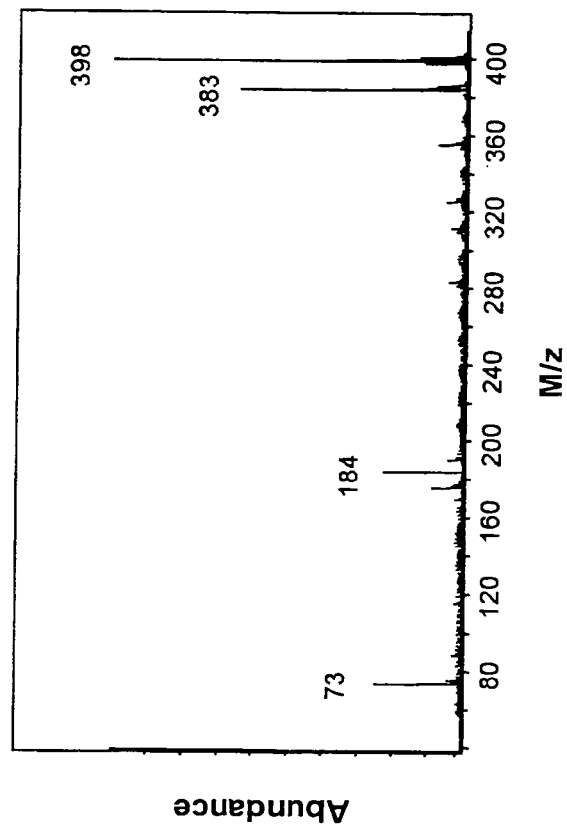

The carbon monoxide difference spectrum of microsomes isolated from insect cells expressing the soybean CYP93C clone indicated the presence of expressed cytochrome P450, as seen from an absorption peak at 450 nm that was not present in similar spectra from insect microsomes originating from cells transformed with a control vector. Unlabeled liquiritigenin was then fed to the microsomes in the presence of NADPH. The substrate remained unconverted in microsomes from cells harboring the control vector. However, in microsomes expressing the CYP93C clone, a new peak of RT 29.96 min was observed by high performance liquid chromatography (FIG. 8A). The amount of this peak was reduced 10-fold if NADPH was omitted from the incubations (FIG. 8B). The UV spectrum of the product, obtained by diode array detection, was identical to that of authentic daidzein ($\lambda$max 248 nm, sh 302 nm, $\lambda$min 222 nm). The product was collected, derivatized, and analyzed by GC-MS. The mass spectrum of the BSTFA derivative was identical to that of an authentic sample of daidzein (FIG. 9). Microsomes containing the CYP93C clone also metabolized naringenin to yield genistein, although somewhat less efficiently than the reaction with liquiritigenin (FIG. 8C). Insect cell microsomes expressing a different soybean cytochrome P450 cDNA, CYP93E, did not convert liquiritigenin to daidzein when incubated in the presence of NADPH (FIG. 8D). These results indicate that the soybean CYP93C encodes IFS.

EXAMPLE 3

Method of Increasing Dietary Isoflavonoid Intake

Transgenic tomato plants are produced by the introduction of CYP93C1v2 via standard *Agrobacterium*-based procedures. In a preferred embodiment, the CYP93C1v2 coding sequence is under control of a gene promoter giving specific expression in the fruit. Progeny containing the coding region of the CYP93C1v2 gene are selected at the seedling stage by standard polymerase chain reaction and/or DNA blot analysis known to those skilled in the art. Plants scoring positive for possession of the transgene are grown to fruiting, and fruit analyzed for the presence of isoflavones by the HPLC methods shown in FIG. 7 and FIG. 8 of the present invention. Fruit harvested from the transgenic tomato plants are ingested to increase the dietary intake of isoflavonoids.

It is to be understood that the above description is of preferred exemplary embodiments of the invention and is intended to be illustrative of the invention, but is not to be construed to limit the scope of the invention in any way. Modifications may be made in the structural features of the invention without departing from the scope of the invention.

In summary, isoflavones can now be genetically engineered to provide potential human health benefits of dietary isoflavones and to increase disease resistance in plants. Isoflavones can now be produced in transgenic plants species in which isoflavones do not naturally occur, i.e., in species other than legumes. For example, engineering constitutive production of daidzein and/or genistein or their conjugates into tomato, potato, corn, or other popular components of the human diet, leads to human health benefits, such as reduced cancer risk, reduced incidence of osteoporosis, and treatment for alcoholism. Alternatively, introducing infection-inducible isoflavonoid biosynthesis into non-legumes qualitatively complements these plants' phytoalexin defenses against microbial pathogens, whereas over-expression of the isoflavonoid pathway in legumes quantitatively increases this defense response. Finally, modifying the extent of production of isoflavonoids in legume roots positively impacts nodulation efficiency and therefore plant yield.

We claim:

1. A method for introducing into a plant the enzyme catalyzing the aryl migration of a flavanone to form an isoflavanone intermediate or an isoflavone, comprising:

introducing a DNA segment encoding said enzyme into said plant to form a transgenic plant, wherein the enzyme comprises more than 97% amino acid identity to the polypeptide encoded by nucleotide 36 to nucleotide 1598 of SEQ ID NO: 1 or nucleotide 92 to nucleotide 1657 of SEQ ID NO:4, wherein said transgenic plant expresses said DNA segment under the control of a suitable constitutive or inducible promoter when said transgenic plant is exposed to conditions which permit expression.

2. The method of claim 1, wherein the plant comprises chalcone synthase, chalcone reductase, and chalcone isomerase genes that are expressed to form liquiritigenin in said plant to cause in vivo formation of daidzein or a daidzein derivative.

3. The method of claim 2, wherein said plant is transformed with said chalcone synthase, chalcone reductase, and chalcone isomerase genes.

4. The method of claim 1 or 2, wherein said plant further comprises downstream genes to metabolize said formed isoflavanone intermediate or isoflavone to biologically active isoflavonoid derivatives or conjugates.

5. The method of claim 4, wherein said downstream genes encode enzymes selected from the group consisting of isoflavone O-methyltransferase, isoflavone 2'-hydroxylase, isoflavone reductase, and vestitone reductase.

6. The method of claim 5, wherein said plant further comprises a down-stream gene encoding 4'-O methyltransferase to form biochanin A or a biochanin A derivative.

7. The method of claim 1, wherein the plant is a naturally isoflavonoid-producing plant, and wherein the plant exhibits increased levels of isoflavonoid compounds from the expression.

8. The method of claim 7, wherein said isoflavonoid is selected from the group consisting of an isoflavonone intermediate, an isoflavone, an isoflavone derivative, and an isoflavone conjugate.

9. The method of claim 1, wherein said DNA segment comprises isolated genomic DNA.

10. The method of claim 1, wherein said DNA segment comprises recombinant cDNA.

11. The method of claim 1, wherein said DNA segment comprises a soybean CYP93C gene.

12. The method of claim 11, wherein said DNA sequence comprises the sequence from nucleotide 36 to nucleotide 1598 of SEQ ID NO: 1.

13. The method of claim 1, said DNA segment is a *Medicago truncatula* homolog of a CYP93C gene.

14. The method of claim 13, wherein said DNA sequence comprises the sequence from nucleotide 92 to nucleotide 1657 of SEQ ID NO: 4.

15. The method of claim 8, wherein said flavanone is liquiritigenin.

16. The method of claim 8, wherein said flavanone is naringenin.

17. The method of claim 1, further comprising isolating an isoflavonoid from the transgenic plant and using it to prepare a food.

18. The method of claim 1, further comprising isolating an isoflavonoid from the transgenic plant and using it to prepare a food stuff, a nutritional supplement, an animal feed supplement, a nutraceutical, or a pharmaceutical.

19. The method of claim 1, wherein said transgenic plant produces an isoflavonoid which provides a pharmaceutical benefit to a patient.

20. A tansgenic plant transformed with an isolated gene or DNA segment which encodes a cytochrome P450 that can catalyze the aryl migration of a flavanone to yield an isoflavanone intermediate or an isoflavone, wherein the cytochrome P450 comprises more than 97% amino acid identity to the polypeptide encoded by nucleotide 36 to nucleotide 1598 of SEQ ID NO: 1 or nucleotide 92 to nucleotide 1657 of SEQ ID NO:4, wherein said transgenic plant exhibits increased levels of an isoflavonoid when compared to the level of said isoflavonoid in plants of the same species which do not comprise said isolated gene or DNA segment.

21. The transgenic plant of claim 20, wherein the level of bacterial or fungal symbiosis is increased.

22. A method of preparing a nutraceutical composition for achieving a nutritional effect using a transgenic plant transformed with an isolated gene or DNA segment which encodes a cytochrome P450 that can catalyze the aryl migration of a flavanone to yield an isoflavanone intermediate or an isoflavone, wherein the cytochrome P450 comprises more than 97% amino acid identity to the polypeptide encoded by nucleotide 36 to nucleotide 1598 of SEQ ID NO: 1 or nucleotide 92 to nucleotide 1657 of SEQ ID NO: 4, wherein said transgenic plant exhibits increased levels of an isoflavonoid when compared to the level of said isoflavonoid in plants of the same species which do not comprise said isolated gene or DNA segment said method comprising transforming a plant with said DNA segment and preparing a nutraceutical composition from said transformed plant.

23. Transformed seed from a transgenic plant comprising at least one recombinant DNA sequence encoding a cytochrome P450 that can catalyze the aryl migration of a flavanone to yield an isoflavanone intermediate or an isoflavone, wherein the cytochrome P450 comprises more than about 97% amino acid identity to the polypeptide encoded by nucleotide 36 to nucleotide 1598 of SEQ ID NO: 1 or nucleotide 92 to nucleotide 1657 of SEQ ID NO:4, wherein the seed comprises the recombinant DNA sequence, wherein said transgenic plant exhibits an increased level of an isoflavonoid when compared to the level of said isoflavonoid in plants of the same species which do not comprise said recombinant DNA sequence.

24. Transformed progeny from a transgenic plant comprising at least one recombinant DNA sequence encoding a cytochrome P450 that can catalyze the aryl migration of a flavanone to yield an isoflavanone intermediate or an isoflavone, wherein the cytochrome P450 comprises more than 97% amino acid identity to the polypeptide encoded by nucleotide 36 to nucleotide 1598 of SEQ ID NO: 1 or nucleotide 92 to nucleotide 1657 of SEQ ID NO:4, wherein the progeny comprises the recombinant DNA sequence, wherein said transgenic plant exhibits an increased level of an isoflavonoid when compared to the level of said isoflavonoid in plants of the same species which do not comprise said recombinant DNA sequence.

25. Transformed progeny from seed of a transgenic plant comprising at least one recombinant DNA sequence encoding a cytochrome P450 that can catalyze the aryl migration of a flavanone to yield an isoflavanone intermediate or an isoflavone, wherein the cytochrome P450 comprises more than 97% amino acid identity to the polypeptide encoded by nucleotide 36 to nucleotide 1598 of SEQ ID NO: 1 or nucleotide 92 to nucleotide 1657 of SEQ ID NO:4, wherein the progeny comprises the recombinant DNA sequence, wherein said transgenic plant exhibits an increased level of an isoflavonoid when compared to the level of said isoflavonoid in plants of the same species which do not comprise said recombinant DNA sequence.

* * * * *